(12) United States Patent
Patil et al.

(10) Patent No.: US 10,683,464 B2
(45) Date of Patent: *Jun. 16, 2020

(54) ESTER COMPOUNDS, LUBRICATING OIL COMPOSITIONS CONTAINING SAME AND PROCESSES FOR MAKING SAME

(71) Applicant: ExxonMobil Chemical Patents Inc., Baytown, TX (US)

(72) Inventors: Abhimanyu O. Patil, Westfield, NJ (US); Kyle G. Lewis, Houston, TX (US); Satish Bodige, Wayne, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/032,223

(22) Filed: Jul. 11, 2018

(65) Prior Publication Data

US 2019/0100711 A1    Apr. 4, 2019

Related U.S. Application Data

(60) Provisional application No. 62/565,536, filed on Sep. 29, 2017.

(51) Int. Cl.
*C10M 129/70* (2006.01)
*C07C 69/003* (2006.01)
(Continued)

(52) U.S. Cl.
CPC ............ *C10M 129/70* (2013.01); *C07C 2/34* (2013.01); *C07C 29/14* (2013.01); *C07C 45/50* (2013.01);
(Continued)

(58) Field of Classification Search
CPC ......... C07C 69/003; C07C 51/14; C07C 2/34; C07C 45/50; C07C 69/24; C07C 69/007;
(Continued)

(56) References Cited

U.S. PATENT DOCUMENTS 2,460,182 A    1/1949  Geigy
3,059,007 A   12/1962  Vos et al.
(Continued)

FOREIGN PATENT DOCUMENTS

DE    10 2013 009323 A    12/2014
EP             0629603        12/1994
(Continued)

OTHER PUBLICATIONS

Sarnayskaya, et al., "Volatility and thermooxidation stability of synthetic ester oils," Khimiya I Tekhnologiya Topliv I Masel, 1975, vol. 10, pp. 49-52 (Abstract).
(Continued)

*Primary Examiner* — Vishal V Vasisth

(57) ABSTRACT

This disclosure relates to ester compounds derived from neo-acids, lubricating oil base stocks comprising such ester compounds, lubricating oil compositions comprising such ester compounds, and method for making such compounds and/or base stocks. The lubricating oil base stocks comprising the ester compounds exhibit desirable lubricating properties such as polarity and oxidation stability.

25 Claims, 2 Drawing Sheets

(51) Int. Cl.

| | |
|---|---|
| C07C 69/24 | (2006.01) |
| C07C 67/08 | (2006.01) |
| C07C 69/007 | (2006.01) |
| C07C 51/14 | (2006.01) |
| C07C 2/34 | (2006.01) |
| C07C 45/50 | (2006.01) |
| C07C 29/14 | (2006.01) |

(52) U.S. Cl.
CPC .............. *C07C 51/14* (2013.01); *C07C 67/08* (2013.01); *C07C 69/003* (2013.01); *C07C 69/007* (2013.01); *C07C 69/24* (2013.01); *C10M 2207/281* (2013.01); *C10M 2207/2815* (2013.01); *C10N 2220/021* (2013.01); *C10N 2220/028* (2013.01); *C10N 2230/02* (2013.01); *C10N 2230/10* (2013.01); *C10N 2230/74* (2013.01)

(58) Field of Classification Search
CPC ......... C07C 67/08; C07C 29/14; C07C 11/02; C07C 51/04; C07C 53/128; C07C 47/02; C07C 31/125; C10N 2230/74; C10N 2230/10; C10N 2220/021; C10N 2220/028; C10N 2230/02; C10M 2207/281; C10M 2207/2815
See application file for complete search history.

(56) References Cited

U.S. PATENT DOCUMENTS

| | | | |
|---|---|---|---|
| 3,910,963 | A | 10/1975 | Souma et al. |
| 4,126,585 | A | 11/1978 | Conrad et al. |
| 4,332,738 | A | 6/1982 | Benitez et al. |
| 4,658,078 | A | 4/1987 | Slaugh et al. |
| 5,646,332 | A | 7/1997 | Cusumano et al. |
| 6,239,318 | B1 | 5/2001 | Schuler et al. |
| 2004/0030168 | A1* | 2/2004 | Mozeleski .............. C07C 67/08 554/174 |
| 2011/0084243 | A1 | 4/2011 | Cranor et al. |
| 2014/0011086 | A1 | 1/2014 | Fujdala et al. |
| 2015/0284350 | A1 | 10/2015 | Aruleswaran et al. |
| 2015/0344805 | A1* | 12/2015 | Dance ................... C10M 157/04 508/293 |
| 2017/0183596 | A1 | 6/2017 | Ng et al. |
| 2018/0119045 | A1 | 5/2018 | Patil et al. |

FOREIGN PATENT DOCUMENTS

| | | |
|---|---|---|
| EP | 2474537 | 7/2012 |
| JP | H0782216 | 3/1995 |
| WO | 2005/049542 | 6/2005 |

OTHER PUBLICATIONS

Pincock et al., "Alkylation of Ethyl, Isobomyl, and Menthyl Esters of 2-Methylbutanoic Acid," Journal of Organic Chemistry, 1964, vol. 29, No. 10, pp. 299-2992.
Pirozkov et al., "Synthesis of allyl esters of neo acids," Shurnal Prikladnol Khimii, 1976, vol. 49, No. 7, pp. 1646-1648 (Abstract).
Shapovalov, et al., "Radiation-induced telomerization of ethylene with methyl propionate," Deposited Doc., Viniti, 1975, vol. 32, No. 8, pp. 1628-1675 (Abstract).
Ye et al., "Nickel-catalyzed directed sulfenylation of sp2 and sp3 C—H bonds," Chemical Communications, 2015, vol. 51, No. 37, pp. 7863-7866.
Prout et al., "Unsymemetrical Quaternary Carbon Compounds. III. The Preparation and Resolution of Trialkylacetic Acids," Journal of Organic Chemistry, 1960, vol. 25, No. 5, pp. 835-838.
U.S. Appl. No. 15/988,716, filed May 24, 2018 Patil et al.
Didomenico et al., "Compounds containing quaternary carbons, their use in medical devices, and methods," PCT Int. Appl., 2003.
Wagner-Jauregg et al., "Cycloalkyl aliphatic acids and their chemotherapeutic trial in leprosy and tuberculosis," Arb. Staatl. Inst. Exptl. Therap. U. Forsch.-Inst. Chemotherap. 1939, Frankfurt, No. 37, pp. 22-27, From: Chem. Zentr., 1939, II, pp. 459-460.
Mndzhoyan etal., "Derivatives of substituted acetic acids. XIX. Synthesis of .beta.-substituted phenylethyl esters of dialkylaminoacetic acids," Doklady Akademii Nauk Armyanskoi SSR, 1959, vol. 29, pp. 235-243.
Re et al., "Cyclization of 3-carboxy-3,6-dimethyl-1,5-heptadiene, a terpene acid with the skeleton of Artemisia ketone," Helvetica Chimica Acta, 1958, vol. 41, pp. 1695-1709.
U.S. Appl. No. 62/565,536, filed Sep. 29, 2017 Patil et al.
Kanth et al., "Selective Reduction of Carboxylic Acids into Alcohols Using NaBH4 nad I2," J. Org. Chem., 1991, vol. 56, pp. 5964-5965.
Prasad et al., "Convenient Methods for the Reduction of Amides, Nitriles, Carboxylic Esters, Acids and Hydroboration of Alkenes Using NaBH4/I2 System," Tetrahedron, 1992, vol. 48, No. 22, pp. 4623-4628.
Jirosova et al., "Sphinganine-Like Biogenesis of (E)-1-Nitropentadec-1-ene in Termite Solders of the Genus *Prorhinotermes*," Chembiochem—a European Journal of Chemical Biology, 2014, vol. 15, No. 4, pp. 533-536.
Luo et al., "Comparative study on aroma compounds in Chinese-type and Japanese-type soy sauces."
Achonduh et al., "From alkenes to alcohols by cobalt-catalyzed hydroformylation-reduction," Tetrahedron, 2015, vol. 71, No. 8, pp. 1241-1246.
Cho et al., "Facile Reduction of Carboxylic Acids, Esters, Acid Chlorides, Amides and Nitriles to Alcohols or Amines Using NaBH4/BF3.Et20," Bulletin of the Korean Chemical Society, 2004, pp. 407-409.
Lebedev et al., "Synthesis of branched carboxylic acids with .alpha.-olefins and carbon monoxide in the presence of boron fluoride dehydrate," Neftepererabotka I Neftekhimiya, 1972, No. 8, pp. 7-11.
Polgar et al., "Long-Chain Acids Containing a Quaternary Carbon Atom, Part II," Journal of the American Chemical Society, 1943, pp. 615-619.
Delrnau et al., "Combined Extraction of Cesium and Strontium from Alkaline Nitrate Solutions," Solvent Extraction and Ion Exchange, 2006, vol. 24, No. 2, pp. 197-217.
Rautenstrauch, "Potassium carboxylates by direct carbonylation of potassium alkoxides," Helvetica Chimica Acta, 1987, vol. 70, No. 3, pp. 593-599.
Newman, "alpha, alpha-Di-t-butyl-beta-propiolactone and Methyldi-t-butylacetic Acid from Di-t-butylketene," The Journal of Organic Chemistry, 1968, pp. 2144-2145.
Asano et al., "Syntheses of branched-chain fatty acids contained in tubercle bacilli. VI. Phyhioic acid. 4," Yakugaku Zasshi, 1945, vol. 65, No. 4A, pp. 15-17.
Churilova et al., "Telomerization of propylene with carboxylic acids," Izvegtiya Akademii Nauk SSSR, Seriya Khimicheskaya, 1975, vol. 11, pp. 2497-2501.
Stallberg-Stenhagen, "Optically active higher aliphatic compounds. XI The synthesis of (−)-2-methyl-2-ethyleicosanoic acid," Arkiv Foer Kemi, 1951, vol. 3, pp. 273-280.
Bondareva et al., "Synthesis and extracting properties of triacylated ethyleneamines," Russian Journal of Applied Chemistry, 2011, vol. 84, No. 11, pp. 1897-1902.
Eidus et al., "Carbonylation of pentene-1 and 3-methylbutene-1 by carbon monoxide in the presence of hydrates of boron trifluoride," Bulletin of the Academy of Sciences of the USSR Division of Chemical Science, 1970, pp. 1585-1587.
U.S. Appl. No. 15/988,683, filed May 24, 2018 Chen et al.

* cited by examiner

ESTER COMPOUNDS, LUBRICATING OIL COMPOSITIONS CONTAINING SAME AND PROCESSES FOR MAKING SAME

PRIORITY CLAIM

This application claims priority to and the benefit of U.S. Ser. No. 62/565,536, filed Sep. 29, 2017, the content of which is incorporated herein by reference in its entirety.

FIELD OF THE DISCLOSURE

This disclosure relates to esters compounds, lubricating oil base stocks, lubricating oil compositions, and processes for making them. In particular, this disclosure relates to ester compounds of neo-acids, lubricating oil base stocks and lubricating oil compositions comprising such ester compounds, and processes for making them.

BACKGROUND OF THE DISCLOSURE

Lubricants in commercial use today are prepared from a variety of natural and synthetic base stocks admixed with various additive packages and solvents depending upon their intended application. The base stocks typically include mineral oils, polyalpha-olefins (PAO), gas-to-liquid (GTL) base oils, silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks admixed with various additive packages.

Polyalpha-olefins (PAOs) are important lubricant base stocks with many excellent lubricant properties, including high viscosity index (VI), low volatility and are available in various viscosity range (e.g., kinematic viscosity at 100° C. in the range of 2 to 300 cSt). However, PAOs are paraffinic hydrocarbons with low polarity. This low polarity leads to low solubility and dispersancy for polar additives or sludge generated during service. To compensate for this low polarity, lubricant formulators usually add one or multiple polar co-base stocks. Ester or alkylated naphthalene (AN) is usually present at 1 to 50 wt % levels in many finished lubricant formulations to increase the fluid polarity which improves the solubility of polar additives and sludge. Furthermore, high oxidation stability is generally desirable for a base stock in order to impart a long service life to engine oils.

Therefore, there is a need for polar base stock fluids that provide appropriate solubility and dispersancy for polar additives or sludge generated during service of lubricating oils as well as a high oxidation stability.

This disclosure meets this and other needs.

SUMMARY OF THE DISCLOSURE

It has been found that esters of neo-acids can be advantageously used as lubricating oil base stocks with desirable lubricating oil properties such as polarity and oxidation stability.

A first aspect of this disclosure relates to a compound having a formula (F-I):

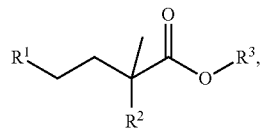

(F-I)

wherein $R^1$ and $R^2$ are each independently a hydrocarbyl group comprising at least two (2) carbon atoms; and $R^3$ is a substituted or unsubstituted hydrocarbyl group.

A second aspect of this disclosure relates to a lubricating oil composition comprising an ester compound of the first aspect of this disclosure.

A third aspect of this disclosure relates to process for making an ester product (such as a lubricating oil base stock) comprising a compound having the following formula (F-I):

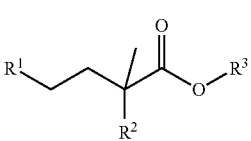

(F-I)

wherein $R^1$ and $R^2$ are each independently a hydrocarbyl group comprising at least two carbon atoms; $R^3$ is a substituted or unsubstituted hydrocarbyl group; the method comprising: reacting a neo-acid having a formula (F-II) and/or an anhydride thereof with an alcohol having a formula (F-III) below in the presence of an acid catalyst to obtain a reaction mixture, where $R^1$, $R^2$, and $R^3$ correspond to the $R^1$, $R^2$, and $R^3$ in formula (F-I), respectively:

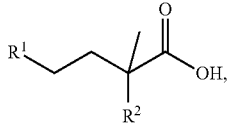

(F-II)

$R^3$—OH (F-III), and obtaining the ester product from the reaction mixture.

Further features and advantages of this disclosure will be understood by reference to the following drawings and detailed description.

DETAILED DESCRIPTION OF THE DISCLOSURE

Definitions

Figure 1:
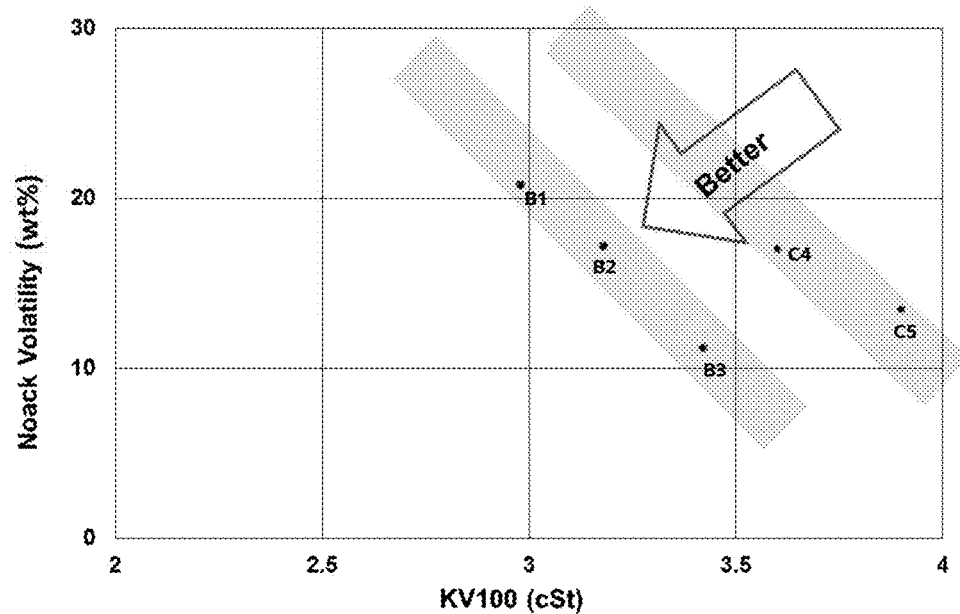
FIG. 1 is a diagram showing the KV100 and Noack volatility of a series of fluids in inventive examples and comparative examples in this disclosure.

In this disclosure, the indefinite article "a" or "an" means at least one, unless it is clearly specified or indicated by the context to mean one.

"Alkyl group" refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms.

"Cycloalkyl group" refers to an alkyl group in which all carbon atoms form a ring structure. Non-limiting examples of cycloalkyl groups include cyclopentyl, cyclohexyl, decahydronaphthalen-1-yl, spiro[5.5]undecan-3-yl, and the like.

"Aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

"Arylalkyl group" refers to an alkyl group substituted by an aryl group or alkylaryl group. Non-limiting examples of arylalkyl group include benzyl, 2-phenylethyl, 4-phenylbutyl, and the like.

"Alkylaryl group" refers to an aryl group substituted by an alkyl group. Non-limiting examples of alkylaryl group include 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, and the like.

"Cycloalkylalkyl group" refers to an alkyl group substituted by a cycloalkyl group or an alkylcycloalkyl group. An example of cycloalkylalkyl group is cyclohexylmethyl, and the like.

"Alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tert-butylcyclohexyl, and the like.

"Hydrocarbyl group" refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic. A "substituted" hydrocarbyl group is a hydrocarbyl group in which a hydrogen atom is substituted by any another group. An "unsubstituted" hydrocarbyl group is a hydrocarbyl group.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

"Mono-ester" refers to a compound having one ester (—C(O)—O—) functional group therein.

"Gamma-branched alcohol" refers to an alcohol having a structure corresponding to the following formula:

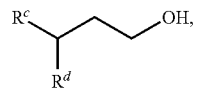

where $R^c$ and $R^d$ are independently linear, branched, cyclic, substituted or unsubstituted hydrocarbyl groups preferably comprising from d1 to d2 carbon atoms, where d1 and d2 can be, independently, 1, 2, 3, 4, 5, 6, 7, 8, 9, 10, 15, 20, 25, 30, 35, 40, 45, 50, 55, 60, 65, 70, 75, 80, 85, 90, 95, 100, as long as d1<d2. More preferably d1=2 and d2=50. Preferably $R^c$ and $R^d$ are alkyl groups. More preferably $R^c$ and $R^d$ are linear or branched alkyl groups. Still more preferably $R^c$ and $R^d$ differ in terms of total number of carbon atoms contained therein by two (2).

"Neo-acid" refers to a carboxylic acid having the following general structure:

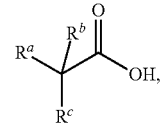

where $R^a$, $R^b$, and $R^c$, the same or different, are independently hydrocarbyl groups.

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Lubricating oil" refers to a substance that can be introduced between two or more surfaces and lowers the level of friction between two adjacent surfaces moving relative to each other. Non-limiting examples of lubricating oils include those in liquid form during normal use thereof such as engine oils and gear box oils and those in viscous liquid form during normal use such as grease. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock may be called a co-base stock.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

All Noack volatility ("NV") values in this disclosure are as determined pursuant to ASTM D5800 unless specified otherwise. Unit of all NV values is wt %, unless otherwise specified.

All percentages in describing chemical compositions herein are by weight unless specified otherwise. "Wt %" means percent by weight.

"Consisting essentially of" means comprising at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

I. The Neo-Acid Ester Compounds

One aspect of this disclosure is a novel category of compounds having a general formula (F 1) below:

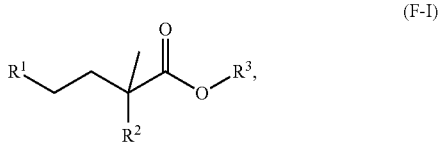

(F-I)

wherein $R^1$ and $R^2$ are each independently a hydrocarbyl group comprising at least 2 carbon atoms therein (preferably a C2 to C60 hydrocarbyl group, more preferably a C2 to C60 alkyl group, still more preferably a C2 to C60 linear or branched alkyl group, still more preferably a C2 to C30 linear or branched alkyl group); and $R^3$ is a substituted or unsubstituted hydrocarbyl group. To the extent this compound can be considered as an ester derived from a neo-acid, it will be referred to as such in this disclosure, and also as "ester of this disclosure" herein.

In formula (F-I), preferably, $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. Preferably c1=2 and c2=30. More preferably c1=2 and c2=24. Still more preferably c1=4, and c2=16. Still more preferably c1=4, and c2=12. Preferably, $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

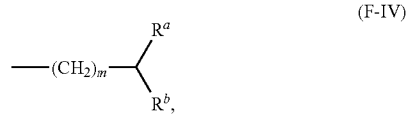

(F-IV)

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably $R^a$ and $R^b$ each independently comprise c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably, the total number of carbon atoms in linear $R^1$ and $R^2$ is an even number. Preferably, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably, the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably, the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ in formula (F-I) differ, it is highly desirable that they differ in terms of molar mass thereof by no greater than 145 (or 130, 115, 100, 85, 70, 55, 45, 30, or even 15) grams per mole. Preferably, in such cases, $R^1$ and $R^2$ differ in terms of total number of carbon atoms contained therein by no greater than 10 (or 9, 8, 7, 6, 5, 4, 3, 2, or even 1).

$R^3$ can be any substituted or unsubstituted hydrocarbyl group. $R^3$ can preferably comprise up to 60, 50, 40, 30, or 20 carbon atoms. Preferably, $R^3$ is a C1-C24 group comprising carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2. Preferably, $R^3$ is a group selected from (a) linear or branched alkyl group, alkylaryl group, aryl group, arylalkyl group, cycloalkyl group, alkylcycloalkyl group, and cycloalkylalkyl group; and (b) substituted derivatives of those in category (a). Substitution to the category (a) hydrocarbyl groups include, but are not limited to: oxygen-containing groups such as alkoxy groups, nitrogen-containing groups, and the like.

Non-limiting examples of $R^3$ as an alkyl group include C1-C24 linear or branched alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, and branched isomeric groups thereof, and the like.

Non-limiting examples of $R^3$ as an aryl group include phenyl, all naphthyls, all phenanthyls, all indenyls, and the like.

Non-limiting examples of $R^3$ as an alkylaryl group include alkyl-substituted phenyls, alkyl-substituted naphthyls, and alkyl substituted phenanthryls. Particular mention can be made of those phenyl groups substituted by an alkyl group such as o, p, and m-methylphenyls, o, p, and m-ethylphenyls, o, p, and m-n-propylphenyls, o, p, and m-n-butylphenyls, o, p, and m-n-pentylphenyls, o, p, and m-n-hexylphenyls, o, p, and m-n-heptylphenyls, o, p, and m-n-octylphenyls, o, p, and m-n-nonylphenyls, o, p, and m-n-decylphenyls, o, p, and m-n-undecylphenyls, o, p, and m-n-dodecylphenyls, o, p, and m-n-tridecylphenyls, o, p, and m-n-tetradecylphenyls, o, p, and m-n-pentadecylphenyls, o, p, and m-n-hexadecylphenyls, o, p, and m-n-heptadecylphenyls, o, p, and m-n-octadecylphenyls; o, p, and m-1-methylmethylphenyls, o, p, and m-1-methylethylphenyls, o, p, and m-1-methylpropylphenyls, o, p, and m-1-methylbutylphenyls, o, p, and m-1-methylpentylphenyls, o, p, and m-1-methylhexylphenyls, o, p, and m-1-methylheptylphenyls, o, p, and m-1-methyloctylphenyls, o, p, and m-1-methylnonylphenyls, o, p, and m-1-methyldecylphenyls, o, p, and m-1-methylundecylphenyls, o, p, and m-1-methyldodecylphenyls, o, p, and m-1-methyltridecylphenyls, o, p, and m-1-methyltetradecylphenyls, o, p, and m-1-methylpentadecylphenyls, o, p, and m-1-methylhexadecylphenyls, o, p, and m-1-methylheptadecylphenyls, and o, p, and m-1-methyloctadecylphenyls.

Non-limiting examples of $R^3$ as an arylalkyl group include: benzyl, 2-phenylethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

Particularly, desirable examples of the ester compounds of this disclosure are as follows, which alone or in combination can be advantageously used as a lubricating oil base stock:

butyl 2-ethyl-2-methylhexanoate; pentyl 2-ethyl-2-methylhexanoate; hexyl 2-ethyl-2-methylhexanoate; heptyl 2-ethyl-2-methylhexanoate; octyl 2-ethyl-2-methylhexanoate; nonyl 2-ethyl-2-methylhexanoate; decyl 2-ethyl-2-methylhexanoate; dodecyl 2-ethyl-2-methylhexanoate; phenyl 2-ethyl-2-methylhexanoate; p-tolyl 2-ethyl-2-methylhexanoate; 3,4-dimethylphenyl 2-ethyl-2-methylhexanoate; 3,5-dimethylphenyl 2-ethyl-2-methylhexanoate; 4-ethylphenyl 2-ethyl-2-methylhexanoate; 4-propylphenyl 2-ethyl-2-methylhexanoate; 4-butylphenyl 2-ethyl-2-methylhexanoate; 4-pentylphenyl 2-ethyl-2-methylhexanoate; 4-hexylphenyl 2-ethyl-2-methylhexanoate; 4-heptylphenyl 2-ethyl-2-methylhexanoate; 4-octylphenyl 2-ethyl-2-methylhexanoate; 4-nonylphenyl 2-ethyl-2-methylhexanoate; naphthalen-2-yl 2-ethyl-2-methylhexanoate; 4-benzylphenyl 2-ethyl-2-methylhexanoate; [1,1'-biphenyl]-4-yl 2-ethyl-2-methylhexanoate;

butyl 2-butyl-2-methyloctanoate; pentyl 2-butyl-2-methyloctanoate; hexyl 2-butyl-2-methyloctanoate; heptyl 2-butyl-2-methyloctanoate; octyl 2-butyl-2-methyloctanoate; nonyl 2-butyl-2-methyloctanoate; decyl 2-butyl-2-methyloctanoate; dodecyl 2-butyl-2-methyloctanoate; phenyl 2-butyl-2-methyloctanoate; p-tolyl 2-butyl-2-methyloctanoate; 3,4-dimethylphenyl 2-butyl-2-methyloctanoate; 3,5-dimethylphenyl 2-butyl-2-methyloctanoate; 4-ethylphenyl 2-butyl-2-methyloctanoate; 4-propylphenyl 2-butyl-2-methyloctanoate; 4-butylphenyl 2-butyl-2-methyloctanoate; 4-pentylphenyl 2-butyl-2-methyloctanoate; 4-hexylphenyl 2-butyl-2-methyloctanoate; 4-heptylphenyl 2-butyl-2-methyloctanoate; 4-octylphenyl 2-butyl-2-methyloctanoate; 4-nonylphenyl 2-butyl-2-methyloctanoate; naphthalen-2-yl 2-butyl-2-methyloctanoate; 4-benzylphenyl 2-butyl-2-methyloctanoate; [1,1'-biphenyl]-4-yl 2-butyl-2-methyloctanoate;

butyl 2-hexyl-2-methyldecanoate; pentyl 2-hexyl-2-methyldecanoate; hexyl 2-hexyl-2-methyldecanoate; heptyl 2-hexyl-2-methyldecanoate; octyl 2-hexyl-2-methyldecanoate; nonyl 2-hexyl-2-methyldecanoate; decyl 2-hexyl-2-methyldecanoate; dodecyl 2-hexyl-2-methyldecanoate; phenyl 2-hexyl-2-methyldecanoate; p-tolyl 2-hexyl-2-methyldecanoate; 3,4-dimethylphenyl 2-hexyl-2-methyldecanoate; 3,5-dimethylphenyl 2-hexyl-2-methyldecanoate; 4-ethylphenyl 2-hexyl-2-methyldecanoate; 4-propylphenyl 2-hexyl-2-methyldecanoate; 4-butylphenyl 2-hexyl-2-methyldecanoate; 4-pentylphenyl 2-hexyl-2-methyldecanoate; 4-hexylphenyl 2-hexyl-2-methyldecanoate; 4-heptylphenyl 2-hexyl-2-methyldecanoate; 4-octylphenyl 2-hexyl-2-methyldecanoate; 4-nonylphenyl 2-hexyl-2-methyldecanoate; naphthalen-2-yl 2-hexyl-2-methyldecanoate; 4-benzylphenyl 2-hexyl-2-methyldecanoate; [1,1'-biphenyl]-4-yl 2-hexyl-2-methyldecanoate;

butyl 2-methyl-2-octyldodecanoate; pentyl 2-methyl-2-octyldodecanoate; hexyl 2-methyl-2-octyldodecanoate; heptyl 2-methyl-2-octyldodecanoate; octyl 2-methyl-2-octyldodecanoate; nonyl 2-methyl-2-octyldodecanoate; decyl 2-methyl-2-octyldodecanoate; dodecyl 2-methyl-2-octyldodecanoate; phenyl 2-methyl-2-octyldodecanoate; p-tolyl 2-methyl-2-octyldodecanoate; 3,4-dimethylphenyl 2-methyl-2-octyldodecanoate; 3,5-dimethylphenyl 2-methyl-2-octyldodecanoate; 4-ethylphenyl 2-methyl-2-octyldodecanoate; 4-propylphenyl 2-methyl-2-octyldodecanoate; 4-butylphenyl 2-methyl-2-octyldodecanoate; 4-pentylphenyl 2-methyl-2-octyldodecanoate; 4-hexylphenyl 2-methyl-2-octyldodecanoate; 4-heptylphenyl 2-methyl-2-octyldodecanoate; 4-octylphenyl 2-methyl-2-octyldodecanoate; 4-nonylphenyl 2-methyl-2-octyldodecanoate; naphthalen-2-yl 2-methyl-2-octyldodecanoate; 4-benzylphenyl 2-methyl-2-octyldodecanoate; [1,1'-biphenyl]-4-yl 2-methyl-2-octyldodecanoate;

butyl 2-decyl-2-methyltetradecanoate; pentyl 2-decyl-2-methyltetradecanoate; hexyl 2-decyl-2-methyltetradecanoate; heptyl 2-decyl-2-methyltetradecanoate; octyl 2-decyl-2-methyltetradecanoate; nonyl 2-decyl-2-methyltetradecanoate; decyl 2-decyl-2-methyltetradecanoate; dodecyl 2-decyl-2-methyltetradecanoate; phenyl 2-decyl-2-methyltetradecanoate; p-tolyl 2-decyl-2-methyltetradecanoate; 3,4-dimethylphenyl 2-decyl-2-methyltetradecanoate; 3,5-dimethylphenyl 2-decyl-2-methyltetradecanoate; 4-ethylphenyl 2-decyl-2-methyltetradecanoate; 4-propylphenyl 2-decyl-2-methyltetradecanoate; 4-butylphenyl 2-decyl-2-methyltetradecanoate; 4-pentylphenyl 2-decyl-2-methyltetradecanoate; 4-heptylphenyl 2-decyl-2-methyltetradecanoate; 4-octylphenyl 2-decyl-2-methyltetradecanoate; 4-nonylphenyl 2-decyl-2-methyltetradecanoate; naphthalen-2-yl 2-decyl-2-methyltetradecanoate; 4-benzylphenyl 2-decyl-2-methyltetradecanoate; [1,1'-biphenyl]-4-yl 2-decyl-2-methyltetradecanoate; and butyl 2-dodecyl-2-methylhexadecanoate; pentyl 2-dodecyl-2-methylhexadecanoate; hexyl 2-dodecyl-2-methylhexadecanoate; heptyl 2-dodecyl-2-methylhexadecanoate; octyl 2-dodecyl-2-methylhexadecanoate; nonyl 2-dodecyl-2-methylhexadecanoate; decyl 2-dodecyl-2-methylhexadecanoate; dodecyl 2-dodecyl-2-methylhexadecanoate; phenyl 2-dodecyl-2-methylhexadecanoate; p-tolyl 2-dodecyl-2-methylhexadecanoate; 3,4-dimethylphenyl 2-dodecyl-2-methylhexadecanoate; 3,5-dimethylphenyl 2-dodecyl-2-methylhexadecanoate; 4-ethylphenyl 2-dodecyl-2-methylhexadecanoatee; 4-propylphenyl 2-dodecyl-2-methylhexadecanoate; 4-butylphenyl 2-dodecyl-2-methylhexadecanoate; 4-pentylphenyl 2-dodecyl-2-methylhexadecanoate; 4-heptylphenyl 2-dodecyl-2-methylhexadecanoate; 4-octylphenyl 2-dodecyl-2-methylhexadecanoate; 4-nonylphenyl 2-dodecyl-2-methylhexadecanoate; naphthalen-2-yl 2-dodecyl-2-methylhexadecanoate; 4-benzylphenyl 2-dodecyl-2-methylhexadecanoate; and [1,1'-biphenyl]-4-yl 2-dodecyl-2-methylhexadecanoate.

Among these, the more preferred examples are as follows, which alone or in combination can be advantageously used as lubricating oil base stocks: pentyl 2-ethyl-2-methylhexanoate; hexyl 2-ethyl-2-methylhexanoate; octyl 2-ethyl-2-methylhexanoate; decyl 2-ethyl-2-methylhexanoate; phenyl 2-ethyl-2-methylhexanoate; p-tolyl 2-ethyl-2-methylhexanoate; 3,4-dimethylphenyl 2-ethyl-2-methylhexanoate; 3,5-dimethylphenyl 2-ethyl-2-methylhexanoate; 4-ethylphenyl 2-ethyl-2-methylhexanoate; 4-propylphenyl 2-ethyl-2-methylhexanoate; 4-butylphenyl 2-ethyl-2-methylhexanoate; 4-pentylphenyl 2-ethyl-2-methylhexanoate; 4-hexylphenyl 2-ethyl-2-methylhexanoate; 4-heptylphenyl 2-ethyl-2-methylhexanoate; 4-octylphenyl 2-ethyl-2-methylhexanoate; 4-nonylphenyl 2-ethyl-2-methylhexanoate; naphthalen-2-yl 2-ethyl-2-methylhexanoate; 4-benzylphenyl 2-ethyl-2-methylhexanoate; [1,1'-biphenyl]-4-yl 2-ethyl-2-methylhexanoate; pentyl 2-butyl-2-methyloctanoate; hexyl 2-butyl-2-methyloctanoate; octyl 2-butyl-2-methyloctanoate; decyl 2-butyl-2-methyloctanoate; phenyl 2-butyl-2-methyloctanoate; p-tolyl 2-butyl-2-methyloctanoate; 3,4-dimethylphenyl 2-butyl-2-methyloctanoate; 3,5-dimethylphenyl 2-butyl-2-methyloctanoate; 4-ethylphenyl 2-butyl-2-methyloctanoate; 4-propylphenyl 2-butyl-2-methyloctanoate; 4-butylphenyl 2-butyl-2-methyloctanoate; 4-pentylphenyl 2-butyl-2-methyloctanoate; 4-hexylphenyl 2-butyl-2-methyloctanoate; 4-heptylphenyl 2-butyl-2-methyloctanoate; 4-octylphenyl 2-butyl-2-methyloctanoate; 4-nonylphenyl 2-butyl-2-methyloctanoate; naphthalen-2-yl 2-butyl-2-methyloctanoate; 4-benzylphenyl 2-butyl-2-methyloctanoate; [1,1'-biphenyl]-4-yl 2-butyl-2-methyloctanoate; pentyl 2-hexyl-2-methyldecanoate; hexyl 2-hexyl-2-methyldecanoate; octyl 2-hexyl-2-methyldecanoate; decyl 2-hexyl-2-methyldecanoate; phenyl 2-hexyl-2-methyldecanoate; p-tolyl 2-hexyl-2-methyldecanoate; 3,4-dimethylphenyl 2-hexyl-2-methyldecanoate; 3,5-dimethylphenyl 2-hexyl-2-methyldecanoate; 4-ethylphenyl 2-hexyl-2-methyldecanoate; 4-propylphenyl 2-hexyl-2-methyldecanoate; 4-butylphenyl 2-hexyl-2-methyldecanoate; 4-pentylphenyl 2-hexyl-2-methyldecanoate; 4-hexylphenyl 2-hexyl-2-methyldecanoate; 4-heptylphenyl 2-hexyl-2-methyldecanoate; 4-octylphenyl 2-hexyl-2-methyldecanoate; 4-nonylphenyl 2-hexyl-2-methyldecanoate; naphthalen-2-yl 2-hexyl-2-methyldecanoate; 4-benzylphenyl 2-hexyl-2-methyldecanoate; [1,1'-biphenyl]-4-yl 2-hexyl-2-methyldecanoate; pentyl 2-methyl-2-octyldodecanoate; hexyl 2-methyl-2-octyldodecanoate; octyl 2-methyl-2-octyldodecanoate; decyl 2-methyl-2-octyldodecanoate; phenyl 2-methyl-2-octyldodecanoate; p-tolyl 2-methyl-2-octyldodecanoate; 3,4-dimethylphenyl 2-methyl-2-octyldodecanoate; 3,5-dimethylphenyl 2-methyl-2-octyldodecanoate; 4-ethylphenyl 2-methyl-2-octyldodecanoate; 4-propylphenyl 2-methyl-2-octyldodecanoate; 4-butylphenyl 2-methyl-2-octyldodecanoate; 4-pentylphenyl 2-methyl-2-octyldodecanoate; 4-hexylphenyl 2-methyl-2-octyldodecanoate; 4-heptylphenyl 2-methyl-2-octyldodecanoate; 4-octylphenyl 2-methyl-2-octyldodecanoate; 4-nonylphenyl 2-methyl-2-octyldodecanoate; naphthalen-2-yl 2-methyl-2-octyldodecanoate; 4-benzylphenyl 2-methyl-2-octyldodecanoate; [1,1'-biphenyl]-4-yl 2-methyl-2-octyldodecanoate; pentyl 2-decyl-2-methyltetradecanoate; hexyl 2-decyl-2-methyltetradecanoate; octyl 2-decyl-2-methyltetradecanoate; decyl 2-decyl-2-methyltetradecanoate; phenyl 2-decyl-2-methyltetradecanoate; p-tolyl 2-decyl-2-methyltetradecanoate; 3,4-dimethylphenyl 2-decyl-2-methyltetradecanoate; 3,5-dimethylphenyl 2-decyl-2-methyltetradecanoate; 4-ethylphenyl 2-decyl-2-methyltetradecanoate; 4-propylphenyl 2-decyl-2-methyltetradecanoate; 4-butylphenyl 2-decyl-2-methyltetradecanoate; 4-pentylphenyl 2-decyl-2-methyltetradecanoate; 4-heptylphenyl 2-decyl-2-methyltetradecanoate; 4-octylphenyl 2-decyl-2-methyltetradecanoate; 4-nonylphenyl 2-decyl-2-methyltetradecanoate; naphthalen-2-yl 2-decyl-2-methyltetradecanoate; 4-benzylphenyl 2-decyl-2-methyltetradecanoate; and [1,1'-biphenyl]-4-yl 2-decyl-2-methyltetradecanoate.

The neo-acid-derived ester compounds of this disclosure can have many applications. One contemplated application is as a base stock of a lubricating oil composition described in detail below. The neo-acid-derived ester compounds of this disclosure can also find use in other fields such as plasticizers, personal care products, heat transfer fluids, hydraulic power transfer oils, processing oils, and the like.

II. The Lubricating Oil Composition Comprising Ester of this Disclosure

II.1 General

In this disclosure, a lubricating oil formulation means a lubricating oil product ready for its intended use. Thus, examples of lubricating oil formulations include: engine oils ready for putting into the crankcase of an internal combustion engine; gear oils ready for being dispensed into a gear box; greases ready for being applied to apparatus in need of greasing; and the like. In this disclosure, a lubricating oil composition can be any portion or the entirety of a lubricating oil formulation. Thus, a lubricating oil composition can be, for example: (i) a base stock; (ii) an additive package comprising one or more additives; (iii) a mixture of two or more base stocks absent any additive; (iv) a mixture of one or more base stocks with one or more additives but not the entirety of a lubricating oil formulation; and (v) a lubricating oil formulation in its entirety.

The esters of this disclosure are useful as base stocks in formulating lubricating oil compositions. To make a final lubricating oil formulation as a product, one may add additional components, such as other base stocks, additional quantities of the materials already present in the lubricating oil composition, additive components, and the like, to the lubricating oil composition. A particularly preferred embodiment of the lubricating oil composition of this disclosure, however, is a lubricating oil formulation.

II.2 Lubricating Oil Base Stocks Comprising Neo-Acid-Derived Ester

The esters of neo-acids of this disclosure have desirable properties such as KV100, KV40, and viscosity index comparable to certain commercial Group V ester-type base stocks. The high polarity of the neo-acid-derived ester molecules as a result of the presence of the ester group lends them excellent blending capabilities with many other base stocks, providing needed solvency and dispersancy of polar components such as additives and sludge formed during the service life of the lubricating oil. The exceptionally high oxidation stability of the neo-acid-derived ester molecules as a result of the location of the ester group connected to a quaternary carbon atom with no hydrogen directly bonded thereto is particularly desirable for a high-performance lubricating oil formulation which is exposed repeatedly to oxidative environment such as automotive engine oils.

The lubricating oil base stock of this disclosure can comprise a single neo-acid-derived ester compound as disclosed above. The concentration of the ester compound in the base stock can be, e.g., at least 80, 90, 95, 98, or even 99 wt %, based on the total weight of the base stock.

The lubricating oil base stock of this disclosure can comprise two or more neo-acid-derived esters as disclosed above. Such base stock can be produced by mixing two ester compounds in their substantially pure form, or produced from a single esterification reaction operation by reacting (i) one neo-acid with two or more alcohols or (ii) two or more neo-acids with one or more alcohols. Such mixed-ester base stock can be particularly advantageous where a mixture of neo-acids (preferably neo-acids with similar molecular weights and/or molecular structures) or a mixture of alcohols (preferably alcohols with similar molecular weights and/or molecular structures) can be procured at a lower cost than a pure single-compound neo-acid product or alcohol product.

The lubricating oil base stock of this disclosure desirably has a KV100 in the range from k1 to k2 cSt, where k1 and k2 can be, independently, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0, as long as k1<k2. Preferably k1=4.0, and k2=30.0. More preferably k1=5.0, and k2=25.0. Therefore, the base stock of this disclosure has a relatively "low" viscosity at the normal operating temperature of an internal combustion engine lubricating oil.

The lubricating oil base stock of this disclosure desirably has a viscosity index as determined pursuant to ASTM D2270 in the range from v1 to v2, where v1 and v2 can be, independently, −100, −90, −80, −70, −60, −50, −40, −30, −20, −10, 0, 10, 20, 30, 40, 50, 60, 70, 80, 90, 100, 110, 120, 130, 140, 150, 160, 170, 180, 190, 200, 210, 220, 230, 240, 250, 260, 270, 290, or 300, as long as v1<v2. Preferably v1=0, and v2=250. More preferably v1=25, and v2=200. Still more preferably v1=100, and v2=170.

The base stock of this disclosure desirably has a NV value in the range from n1 to n2 wt %, where n1 and n2 can be, independently, 0, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, or 90, as long as n1<n2. Preferably n1=0 and n2=50. More preferably n1=0 and n2=30. Still more preferably n1=0 and n2=20. Still more preferably n1=0 and n2=16. In general, for the same type of neo-acid-derived ester base stock, the larger the molecular weight of the molecule, the lower the NV value. For engine oils and base stocks for them, typically a low NV value is preferred, all other parameters held equal.

The base stock of this disclosure desirably have an aniline value as determined by ASTM D611 of no higher than 30, 25, 20, or 15.

Gamma-branched alcohols-derived esters are demonstrated as good quality lubricating oil base stocks. In a surprising manner, it has been found that selective base stocks of this disclosure based on neo-acid-derived esters perform better than gamma-branched alcohols-derived ester base stocks having at the same molecular weight and with comparable molecular structure. In particular, it has been found that selective ester base stocks of this disclosure tend to have significantly higher oxidation stability compared to gamma-alcohol-derived esters having the same molecular weight and/or similar KV100.

Moreover, compared to PAO base stocks at similar viscosity (KV100, in particular), the base stock of this disclosure comprising a neo-acid-derived ester tend to have higher polarity and lower volatility (NV value, in particular).

The neo-acid-derived ester base stock of this disclosure can be used as a primary base stock or a co-base stock in any lubricating oil formulation. Preferably, the neo-acid-derived ester base stock of this disclosure is used as a co-base stock in conjunction with a second base stock designated as a primary base stock. In certain applications, it may be desirable to include two or even more additional base stocks in the lubricating oil formulation, in addition to the neo-acid-derived ester base stock of this disclosure. For the convenience of description, the neo-acid-derived ester base stock is merely referred to as a generic base stock herein, regardless of its primary base stock or co-base stock designation. The base stock of this disclosure comprising a neo-acid-derived ester can be particularly advantageous when used as a co-base stock with a non-polar base stock such as those Group I, II, III, GTL, and Group IV base stocks.

The neo-acid-derived ester base stocks of this disclosure are preferably used for formulating automobile engine lubricating oils, preferably those meeting the SAE J300 classification standards. However, it is contemplated that the base stocks of this disclosure may be used to formulate other lubricating oils (e.g., automobile drive-line oils, industrial lubricating oils, gear oils, greases, and the like), heat transfer oils (e.g., transformer oils), hydraulic power transfer oils, processing oils, and the like.

The neo-acid-derived ester base stock can be present in the lubricating oil formulation of this disclosure in an amount from about c1 to c2 wt %, based on the total weight of the lubricating oil composition, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, or 95, as long as c1<c2. Preferably c1=3, and c2=50. More preferably c1=5, and c2=30. In general, it is desirable that the lubricating oil composition contains the neo-acid-derived ester base stock as a co-base stock. However, it is also contemplated that the lubricating oil formulation of this disclosure may contain the neo-acid derived ester base stock as a primary base stock, and in an extreme case, the lubricating oil formulation may consist essentially of a neo-acid derived ester base stock and additives.

Owing to the high polarity of the neo-acid-derived ester base stocks resulting from the ester group in their molecular structures, the lubricating oil compositions of this disclosure can have an improved additive and sludge solvency and dispersancy compared to other lubricating oil compositions free of ester-type base stocks. In addition, a lubricating oil composition including a neo-acid-derived ester base stock can have improved seal compatibility compared to compositions free of ester-type base stocks.

II.3 Other Base Stocks Useful in the Lubricating Oil Compositions

A wide range of lubricating oil base stocks known in the art can be used in conjunction with the neo-acid-derived ester base stock in the lubricating oil compositions of this disclosure, as a primary base stock or a co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, IV and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalpha-olefins (PAO). Group V base stocks include base stocks not included in Groups I-IV. The table below summarizes properties of each of these five groups.

| Base Stock Properties | | | |
| --- | --- | --- | --- |
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | PAO products | | |
| Group V | All other products not included in Groups I, II, III, and IV | | |

Natural oils include animal oils (e.g., lard), vegetable oils (e.g., castor oil), and mineral oils. Animal and vegetable oils possessing favorable thermal oxidation stability can be used. Of the natural oils, mineral oils are preferred. Mineral oils vary widely as to their crude source, e.g., as to whether they are paraffinic, naphthenic, or mixed paraffinic-naphthenic. Oils derived from coal or shale are also useful in this disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalpha-olefins ("PAO") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, United States.

All other synthetic base stocks, including but not limited to alkyl aromatics and synthetic esters are in Group V.

Additional esters not in the neo-acid-derived ester category in a minor amount may be useful in the lubricating oil compositions of this disclosure. Additive solvency and seal compatibility characteristics may be further imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following may be used as a base stock in the lubricating oil of this disclosure as well: (1) one or more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks preferably comprise linear or branched hydrocarbyl compounds of C20 or higher, more preferably C30 or higher.

The lubricating oil compositions of this disclosure can comprise one or more Group I, II, III, IV, or V base stocks in addition to the neo-acid-derived ester base stock. Preferably, Group I base stocks, if any, are present at a relatively low concentration if a high quality lubricating oil is desired. Group I base stocks may be introduced as a diluent of an additive package at a small quantity. Groups II and III base stocks can be included in the lubricating oil compositions of this disclosure, but preferably only those with high quality, e.g., those having a VI from 100 to 120. Group IV and V base stocks, preferably those of high quality, are desirably included into the lubricating oil compositions of this disclosure.

II.4 Lubricating Oil Additives

The lubricating oil composition of this disclosure may additionally contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N J (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalphaolefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Colum 39, line 68; (c) U.S. Pat. No. 9,422,497 B2, Column 34, line 4 to Colum 40, line 55; and (d) U.S. Pat. No. 8,048,833 B2, Column 17, line 48 to Colum 27, line 12, the disclosures of which are incorporated herein in their entirety. These additives are commonly delivered with varying amounts of diluent oil that may range from 5 wt % to 50 wt % based on the total weight of the additive package before incorporation into the formulated oil. The additives useful in this disclosure do not have to be soluble in the lubricating oil compositions. Insoluble additives in oil can be dispersed in the lubricating oil compositions of this disclosure.

When lubricating oil compositions contain one or more of the additives discussed above, the additive(s) are blended into the lubricating oil composition in an amount sufficient for it to perform its intended function.

It is noted that many of the additives are shipped from the additive manufacturer as a concentrate, containing one or more additives together, with a certain amount of base oil diluents.

III. Method for Making the Ester Products Comprising Neo-Acid Ester Compounds and Lubricating Oil Base Stock Comprising the Same One aspect of this disclosure relates to a process for making (i) an ester product comprising a compound having the following formula (I) and/or specifically, (ii) a lubricating oil base stock comprising a compound having the following formula (F-I):

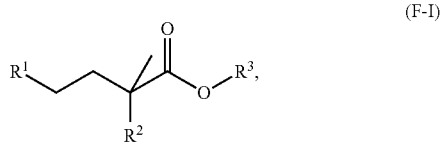

(F-I)

wherein: $R^1$ and $R^2$ are each independently a hydrocarbyl group comprising at least two (2) carbon atoms (preferably a C2-C60 hydrocarbyl group, more preferably a C2-C60 alkyl group, still more preferably a C2-C60 linear or branched alkyl group, still more preferably a C2 to C30 linear or branched alkyl group); $R^3$ is a hydrocarbyl group; the method comprising:
reacting a neo-acid having formula (F-II) and/or an anhydride thereof with an alcohol having a formula (F-III) below in the presence of an acid catalyst to obtain a reaction mixture, where $R^1$, $R^2$ and $R^3$ correspond to the $R^1$, $R^2$, and $R^3$ in formula (F-I), respectively:

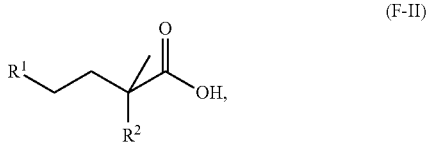

(F-II)

obtaining the ester product or the lubricating oil base stock from the reaction mixture.

It is highly desirable that the acid/anhydride used in the reaction are those of a single mono-acid for the purpose of making a single compound having formula (I), an ester product (such as a lubricating oil base stock) comprising one or more compound(s) having formula (I), although those of multiple acids can be used as well, especially for the purpose of making an ester product or a lubricating oil base stock which can comprise a mixture of multiple, different compounds each having a molecular structure represented by formula (I).

In formula (F-I), preferably, $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. Preferably, c1=2 and c2=30. More preferably c1=2 and c2=24. Still more preferably c1=4, and c2=16. Preferably $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

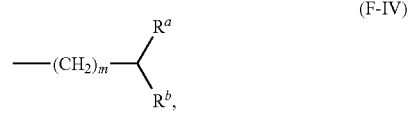

(F-IV)

where $R^a$ and $R^b$ are independently hydrocarbyl groups, preferably alkyl groups, still more preferably, linear or branched alkyl groups, still more preferably linear alkyl groups, m is a non-negative integer, preferably m≥2, more preferably m≥3, still more preferably, m≥4, still more preferably m≥5, still more preferably m≥6, still more preferably m≥7. Preferably $R^a$ and $R^b$ independently comprises c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably the total number of carbon atoms in linear $R^1$ and $R^2$ is an even number. Preferably the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably, the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ differ, it is highly desirable that they differ in terms of molar mass thereof by no greater than 145 (or 130, 115, 100, 85, 70, 55, 45, 30, or even 15) grams per mole. Preferably, in such cases, $R^1$ and $R^2$ differ in terms of total number of carbon atoms contained therein by no greater than 10 (or 9, 8, 7, 6, 5, 4, 3, 2, or even 1).

$R^3$ can be any substituted or unsubstituted hydrocarbyl group. $R^3$ can preferably comprise up to 60, 50, 40, 30, or 20 carbon atoms. Preferably, $R^3$ is a C1-C24 group comprising carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2. Preferably, $R^3$ is a group selected from (a) linear or branched alkyl group, alkylaryl group, aryl group, arylalkyl group, cycloalkyl group, alkylcycloalkyl group, and cycloalkylalkyl group; and (b) substituted derivatives of those in category (a). Substitution to the category (a) hydrocarbyl groups include, but are not limited to: oxygen-containing groups such as alkoxy groups, nitrogen-containing groups, and the like.

Non-limiting examples of $R^3$ as an alkyl group include C1-C24 linear or branched alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, and branched isomeric groups thereof, and the like.

Non-limiting examples of $R^3$ as an aryl group include phenyl, all naphthyls, all phenanthyls, all indenyls, and the like.

Non-limiting examples of $R^3$ as an alkylaryl group include alkyl-substituted phenyls, alkyl-substituted naphthyls, and alkyl substituted phenanthryls. Particular mention can be made of those phenyl groups substituted by an alkyl group such as o, p, and m-methylphenyls, o, p, and m-ethylphenyls, o, p, and m-n-propylphenyls, o, p, and m-n-butylphenyls, o, p, and m-n-pentylphenyls, o, p, and m-n-hexylphenyls, o, p, and m-n-heptylphenyls, o, p, and m-n-octylphenyls, o, p, and m-n-nonylphenyls, o, p, and m-n-decylphenyls, o, p, and m-n-undecylphenyls, o, p, and m-n-dodecylphenyls, o, p, and m-n-tridecylphenyls, o, p, and m-n-tetradecylphenyls, o, p, and m-n-pentadecylphenyls, o, p, and m-n-hexadecylphenyls, o, p, and m-n-heptadecylphenyls, o, p, and m-n-octadecylphenyls; o, p, and m-1-methylmethylphenyls, o, p, and m-1-methylethylphenyls, o, p, and m-1-methylpropylphenyls, o, p, and m-1-methylbutylphenyls, o, p, and m-1-methylpentylphenyls, o, p, and m-1-methylhexylphenyls, o, p, and m-1-methylheptylphenyls, o, p, and m-1-methyloctylphenyls, o, p, and m-1-methylnonylphenyls, o, p, and m-1-methyldecylphenyls, o, p, and m-1-methylundecylphenyls, o, p, and m-1-methyldodecylphenyls, o, p, and m-1-methyltridecylphenyls, o, p, and m-1-methyltetradecylphenyls, o, p, and m-1-methylpentadecylphenyls, o, p, and m-1-methylhexadecylphenyls, o, p, and m-1-methylheptadecylphenyls, and o, p, and m-1-methyloctadecylphenyls.

Non-limiting examples of $R^3$ as an arylalkyl group include: benzyl, 2-phenylethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

The neo-acid product useful in the process for making the ester products of this disclosure can be made from a process comprising the following steps: (Ia) providing a vinylidene olefin feed comprising a vinylidene olefin having the following formula (F-III):

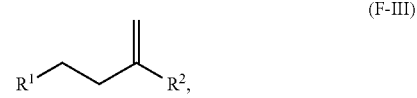

(F-III)

where $R^1$ and $R^2$ correspond to the $R^1$ and $R^2$ in formula (F-I); (Ib) contacting the vinylidene olefin with carbon monoxide in a reactor in the presence of an acid catalyst (preferably at a carbon monoxide partial pressure of at least 1.0 MPa, more preferably at least 3.5 MPa, still more preferably at least 5.0 MPa) to obtain a reaction mixture; (Ic) contacting the reaction mixture with water to obtain an acid product mixture; and (Id) obtaining at least a portion of the neo-acid product from the crude acid mixture.

The vinylidene olefin feed useful in step (Ia) above can be advantageously made from a terminal olefin monomer feed in a process comprising the following steps: (Ia.1) providing a monomer feed comprising a terminal olefin having a formula (F-V) below and a terminal olefin having a formula (F-VI) below: $R^1$—CH═$CH_2$ (F-V); $R^2$—CH═$CH_2$ (F-VI); where $R^1$ and $R^2$ correspond to the $R^1$ and $R^2$ in formulas (F-III), (F-II) and (F-I), respectively; (Ia.2) oligomerizing the monomer feed in an oligomerization reactor in the presence of a catalyst system comprising a metallocene compound to obtain an oligomerization product mixture; and (Ia.3) obtaining at least a portion of the vinylidene olefin feed from the oligomerization product mixture. In this process where $R^1$ and $R^2$ in formula (F-I) of the neo-alcohol are identical, a single terminal olefin having formula (F-V) is used in the monomer feed. Where $R^1$ and $R^2$ in formula (F-I) of the neo-alcohol are different, at least two terminal olefins having different formulas (F-V) and (F-VI) are used in the monomer feed. In case two different terminal olefins are used in the monomer feed, the oligomerization product mixture obtainable from step (Ia.2) may comprise up to four vinylidene olefins as dimers of the two terminal olefins, which may be separated to obtain the desirable vinylidene olefin feed in step (Ia.3) comprising one, two, three, or all four vinylidene olefins, as the case may be. Nine vinylidene olefin dimers can result from three different terminal olefins in the monomer feed. These different vinylidene olefins, if contained in the vinylidene olefin feed in step (Ia) of the process for making the neo-acid described above, can be converted into corresponding neo-acids in the neo-acid product, which, in turn, can be converted into corresponding ester compounds in the neo-acid-derived ester product.

The above processes for making neo-acid product starting from terminal olefin monomer via the vinylidene olefin intermediate can be illustrated in the following Scheme-I:

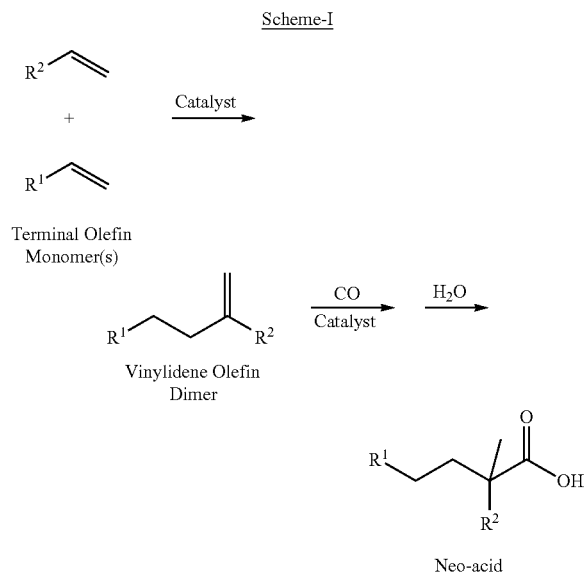

Only one type of vinylidene olefin dimer is illustrated in Scheme-I above. Specific examples of Scheme-I is provided in Part A of the Examples in this disclosure Co-pending, co-assigned U.S. Provisional Patent Application No. 62/551,081 (entitled "Process for Making Vinylidene Olefin" and having a filing date of Aug. 28, 2017) discloses vinylidene olefin dimers of terminal olefins useful for making neo-acids suitable for making neo-alcohols of this disclosure and processes for making such vinylidene dimers, the content of which is incorporated herein by reference in its entirety.

Non-limiting examples of neo-acids useful in the process of this disclosure include the following: 2-ethyl-2-methylhexanoic acid; 2-methyl-2-propylheptanoic acid; 2-butyl-2-methyloctanoic acid; 2-methyl-2-pentylnonanoic acid; 2-hexyl-2-methyldecanoic acid; 2-heptyl-2-methylundecanoic acid; 2-methyl-2-octyldodecanoic acid; 2-decyl-2-methyltetradecanoic acid; 2-dodecyl-2-methylhexadecanoic acid; 2-methyl-2-tetradecyloctadecanoic acid; and 2-methyl-2-hexadecylicosanoic acid.

Co-pending, co-assigned U.S. Provisional Application Ser. No. 62/565,560 filed Sep. 29, 2017 (2017EM311) discloses neo-acids suitable for use in the process of this disclosure for making neo-acid-derived esters and processes for making neo-acids, the content of which is incorporated herein by reference in its entirety.

The anhydrides of the neo-acid can be prepared from a corresponding neo-acid having a formula (F-II) by, e.g., dehydration. Dehydration can be achieved by, e.g., reacting with dehydration agents such as $P_2O_5$, followed by separation.

In the process for making the ester of this disclosure, either the neo-acid having a formula (F-II), or its anhydride, or a mixture thereof, can be used to react with the alcohol having a formula (F-III).

In the alcohol having a formula (F-III), $R^3$ corresponds to the $R^3$ in formula (F-I) as described above.

Particularly, desirable examples of the alcohol useful in the process of this disclosure are as follows: ethanol; propan-1-ol; butan-1-ol; pentan-1-ol; hexan-1-ol; heptan-1-ol; octan-1-ol; nonan-1-ol; decan-1-ol; undecan-1-ol; dodecan-1-ol; tridecan-1-ol; tetradecan-1-ol; pentadecan-1-ol; hexadecane-1-ol; septadecan-1-ol; octadecan-1-ol; nonadecan-1-ol; icosan-1-ol; benzyl alcohol; 2-phenylethanol; 3-phenyl-propan-1-ol; 4-phenyl-butan-1-ol; 5-phenyl-pentan-1-ol; 6-phenyl-hexan-1-ol; 7-phenyl-heptan-1-ol; 8-phenyl-octan-1-ol; 9-phenyl-nonan-1-ol; and 10-phenyl-decan-1-ol.

It is highly desirable that a single alcohol having formula (F-III) is used in the esterification reaction to produce a single ester of this disclosure and/or a lubricating oil base stock comprising a single ester compound of this disclosure. In such case, if an acid/anhydride of a single mono-acid is used, a high-purity ester compound having a formula (F-I) can be obtained and used as a lubricating oil base stock. This is illustrated in Examples B1, B2, and B3 in this disclosure.

It is also contemplated that multiple alcohols can be used in the esterification reaction. In the case where two different alcohols and the acid/anhydride of a single mono-acid are used in the reaction, the reaction mixture will comprise two different ester compounds. The ratio between the quantities of two ester compounds can change as a function of the ratio between the quantities of the two alcohols used. In certain situations, where a mixture of alcohols having similar molecular weights and structures can be procured at a lower cost than a pure alcohol compound, this embodiment can be highly economic to produce a mixture of ester compounds with similar molecular structures, molecular weights, and properties suitable as a lubricating oil base stock product.

The catalyst used in the reaction can be an acid, desirably a strong acid. Non-limiting examples of such acid are: p-toluenesulfonic acid monohydride (PTSA), titanium isopropoxide and sulfuric acid.

The reaction can be advantageously carried out in the presence of a solvent. The specific solvent used is not critical as long as it is inert in the reaction. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The reaction mixture from the esterification reaction typically comprises the intended ester product(s), water, and one or more of unreacted acid/anhydride and alcohol, and byproducts such as ethers and esters of the acid catalyst. Continuous removal of water from the reaction system can result in higher yield of the ester product. Components in the reaction mixture having a boiling point lower than the intended neo-acid-derived ester can be removed by flashing. Depending on the reactants used and reaction conditions, purification methods such as solvent extraction, chromatography, distillation, and the use of sorbents can be carried out to remove byproducts from reaction mixture to finally obtain an ester product of this disclosure comprising a single compound of formula (F-I) or a mixture of multiple compounds of formula (F-I), which can be used as a base stock product, or combined with other, similar compounds to form a base stock product. Preferably, the neo-acid ester product obtainable from the process of this disclosure consists essentially of one or more neo-acid-derived ester compounds. More preferably, the neo-acid ester product obtainable from the process of this disclosure comprises neo-acid-derived ester compounds at a total concentration thereof, based on the total weight of the neo-acid ester product, at least 95 wt %, or at least 98 wt %, or even at least 99 wt %. Preferably, the neo-acid ester product obtainable from the process of this disclosure consists essentially of one predominant neo-acid-derived ester compound. More preferably, the neo-acid ester product obtainable from the process of this disclosure comprises a predominant neo-acid-derived ester compound at a concentration thereof, based on the total weight of the neo-acid ester product, of at least 95 wt %, or at least 98 wt %, or even at least 99 wt %.

This disclosure is further illustrated by the following non-limiting examples.

EXAMPLES

In the following examples, kinematic viscosity at 100° C. ("KV100") and 40° C. ("KV40") of fluids were determined pursuant to ASTM standards D-445; viscosity index ("VI") was determined pursuant to ASTM standard D-2270; and Noack volatility ("NV") were determined using thermal gravimetric analysis ("TGA").

Part A: Synthesis of 2-Methyl-2-octyldodecanoic Acid

Example A1: Synthesis of 9-methylenenonadecane

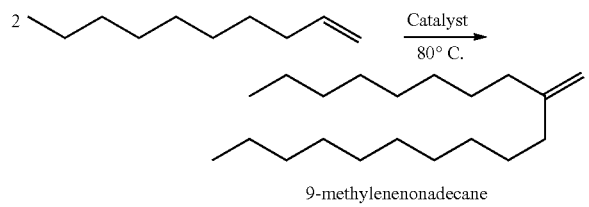

9-methylenenonadecane

Into a batch reactor was charged 5000 grams of 1-decene (98.6% 1-decene, 0.7% 1-octene, 0.7% 1-dodecene), into which 50 grams of 10% methylalumoxane ("MAO") solution was added and held for 60 minutes at 80° C. 450 grams of catalyst solution (1.4 wt % biscyclopentadienyl zirconium (IV) dichloride dissolved in toluene) was subsequently added over 52 minutes. The reactor was held at 80° C. for 6 hours before the reaction was cooled and quenched with 10 ml of water. Gas chromatography showed reactor conversion was 74% with 88% selectivity to dimer and 12% selectivity to trimer and heavier species.

Filter aid was added thereafter into the fluid, which was filtered to remove Zr and/or Al-containing solid particles. The resultant mixture was then flashed to remove the residual monomer and distilled to remove heavies product to isolate the dimer species. The recovered dimer product was measured to contain dimers of the starting olefin at a concentration of 99.5 wt % by GC and a concentration of 9-methylenenonadecane at 98 mol % (by $^1$H NMR).

Example A2: Synthesis of 2-Methyl-2-octyldodecanoic Acid

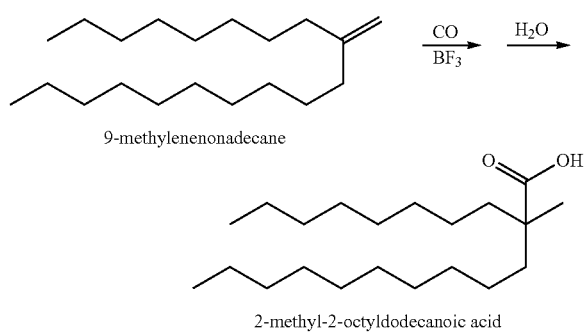

Into a 1-gallon (3.78-liter) autoclave, 1204 grams of the dimer product obtained from Example B1 above was added. Then 613 grams of BF$_3$-dihydrate was added with stirring and cooling. The reactor was then pressurized to 1000 psig with CO. Afterwards an additional 330 grams of BF$_3$ was bubbled into the reactor. The reactor was then pressurized to 2000 psig (13.79 MPa, gauge pressure) by CO and the temperature of the reactor increased to 50° C. The reaction was allowed to continue for 22 hours at the same CO pressure and the same temperature. Afterwards, the reactor was depressurized and allowed to cool to 30° C.

The reaction mixture was then pressured into a 12-liter flask containing 4 liters of water. Nitrogen gas was bubbled through the mixture for 3 hours to remove residual BF$_3$. Excess water was then drained off. The resultant mixture was then water washed seven (7) times, each time using one (1) liter of deionized water to remove the residual catalyst. Residual water in the resultant mixture was subsequently removed from with a rotary evaporator to obtain a crude product.

The total conversion of the vinylidene olefin in the carboxylation step was measured (by gas chromatography) to be 90.7%, with a yield to heavy dimer species of the vinylidene olefin measured to be 6.6%, and thus a yield to the desired neo-acid product at 84.1%.

The crude product was then batch distilled to remove lights (unreacted vinylidene olefin) and heavies to obtain a final neo-acid product. Gas chromatography of the final neo-acid product showed a concentration of neo-acid of about 98% and a concentration of heavy components of about 2%.

The final neo-acid product was measured to have a KV100 of 8.51 cSt, and a KV40 of 64.0 cSt. $^{13}$C-NMR spectra indicates that the final neo-acid product contained 2-methyl-2-octyldodecanoic acid at a purity of 98.1 wt %.

Part B: Synthesis of Various Esters of 2-Methyl-2-octyldodecanoic Acid

Example B1: Synthesis of Pentyl 2-Methyl-2-octyldodecanoate

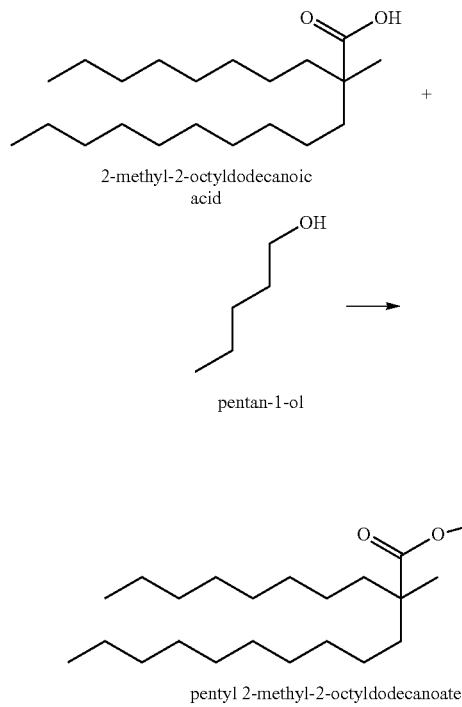

Into a 250 ml glass reactor fitted with an Argon purge was placed 2-methyl-2-octyldodecanoic acid (32.7 grams, 0.1 moles, the final neo-acid product made pursuant to Example A2), 1-pentanol (26.5 grams, 0.3 moles) and p-toluene sulfonic acid monohydrate (21 grams, 0.11 moles). The mixture above was purged with Argon at room temperature for one hour. The mixture was heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10% aqueous NaHCO$_3$ followed by 250 ml saturated aqueous NaCl. The ethyl acetate solution was dried over MgSO$_4$ and then filtered. The ethyl acetate was then removed on a rotary evaporator. The residue was placed on a Kugelrohr vacuum distillation device where the ester was distilled to obtain a final ester product. The weight of the final ester product was 25.7 grams. The final ester product was characterized by $^1$HNMR, $^{13}$CNMR and IR. $^1$H NMR (CDCl$_3$): δ 3.98 (t, 2H, O—CH$_2$—), 1.53 (m, 4H—CH$_2$—) 1.24-1.04 (m, 31H, —CH$_3$, —CH$_2$—), 0.80 (t, 9H, —CH$_3$). $^{13}$C NMR (CDCl$_3$): 177.57, 64.11, 54.92, 39.53, 31.90, 31.87, 30.18, 29.61, 29.52, 29.47, 29.37, 29.27, 29.38, 28.20, 24.56, 22.66, 22.64, 22.28, 21.06, 14.04.

Example B2. Synthesis of Hexyl 2-Methyl-2-octyldodecanoate

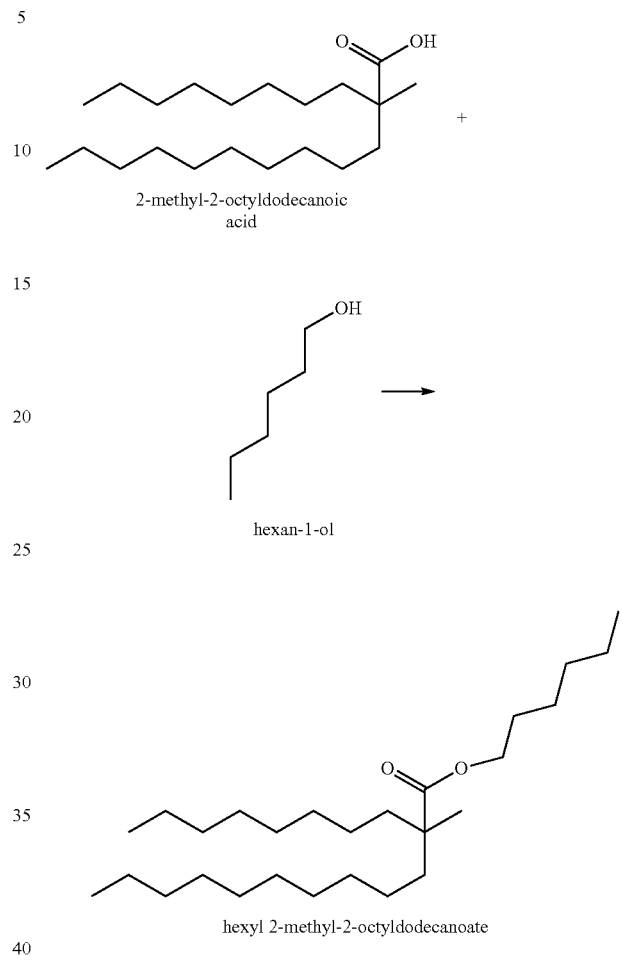

Into a 250 ml glass reactor fitted with an Argon purge was placed 2-methyl-2-octyldodecanoic acid (32.7 grams, 0.1 moles, the final neo-acid product of made pursuant to Example A2), 1-hexanol (20.4 grams, 0.2 moles) and p-toluene sulfonic acid monohydrate (21 grams, 0.11 moles). The mixture above was purged with Argon at room temperature for one hour. The mixture was heated to 100° C. under Argon purge for 18 hours. The mixture was then cooled to room temperature. The residue was dissolved into 100 ml with ethyl acetate and placed into a separatory funnel. The ethyl acetate solution was then extracted once with 100 ml of distilled water. The ethyl acetate layer was then washed with 250 ml 10% aqueous NaHCO$_3$ followed by 250 ml saturated aqueous NaCl. The ethyl acetate solution was dried over MgSO$_4$ and then filtered. The ethyl acetate was removed on a rotary evaporator. The residue was placed on a Kugelrohr vacuum distillation device where the ester was distilled to obtain a final ester product. The weight of the final ester product was 27 grams. The final ester product was characterized by $^1$H NMR, $^{13}$C NMR. $^1$H NMR (CDCl$_3$): δ 3.98 (t, 2H, O—CH$_2$—), 1.53 (m, 4H—CH$_2$—) 1.24-1.04 (m, 39H, —CH$_3$, —CH$_2$—), 0.80 (t, 9H, CH$_3$). $^{13}$C NMR (CDCl$_3$): 177.82, 63.97, 46.07, 39.62, 31.92, 31.88, 31.42, 30.19, 29.62, 29.50, 29.33, 29.30, 28.65, 25.72, 24.58, 22.69, 22.59, 21.12, 14.10.

Example B3. Synthesis of Octyl 2-methyl-2-octyldodecanoate

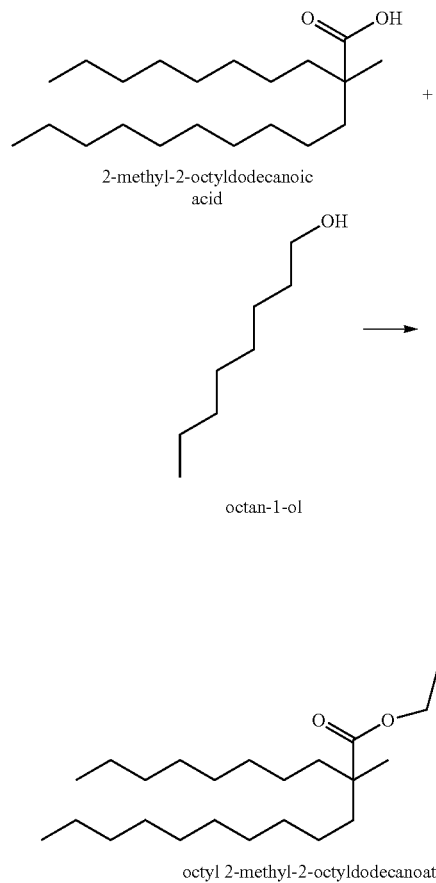

2-methyl-2-octyldodecanoic acid octan-1-ol octyl 2-methyl-2-octyldodecanoate

Into a 250 ml glass reactor fitted with an Argon purge was placed 2-methyl-2-octyldodecanoic acid (32.7 grams, 0.1 moles), 1-octanol (39.1 grams, 0.3 moles) and p-toluene sulfonic acid monohydrate (21 grams, 0.11 moles). The mixture above was purged with Argon at room temperature for one hour. The mixture was heated to 100° C. under Argon purge for 18 hours. The mixture was then cooled to room temperature. The residue was dissolved into 100 ml with ethyl acetate and placed into a separatory funnel. The ethyl acetate solution was then extracted once with 100 ml of distilled water. The ethyl acetate layer was then washed with 250 ml 10% aqueous $NaHCO_3$ followed by 250 ml saturated aqueous NaCl. The ethyl acetate solution was dried over $MgSO_4$ and then filtered. The ethyl acetate was then removed on a rotary evaporator. The residue was placed on a Kugelrohr vacuum distillation device where the ester was distilled to obtain a final ester product. The weight of the final ester product was 28.5 grams. The final ester product was characterized by $^1H$ NMR, $^{13}C$ NMR. $^1H$ NMR ($CDCl_3$): δ 3.98 (t, 2H, O—$CH_2$—), 1.53 (m, 4H—$CH_2$—) 1.24-1.04 (m, 43H, —$CH_3$, —$CH_2$—), 0.80 (t, 9H, —$CH_3$). $^{13}C$ NMR ($CDCl_3$): 177.63, 64.15, 45.94, 39.55, 31.92, 31.89, 31.81, 30.20, 29.63, 29.54, 29.35, 29.29, 29.25, 29.22, 28.70, 26.06, 24.58, 23.92, 22.67, 22.55.

Part C: Synthesis of Various Esters of 3-Octyltridecan-1-ol (Comparative)

Example C0. Synthesis of 3-Octyltridecan-1-ol

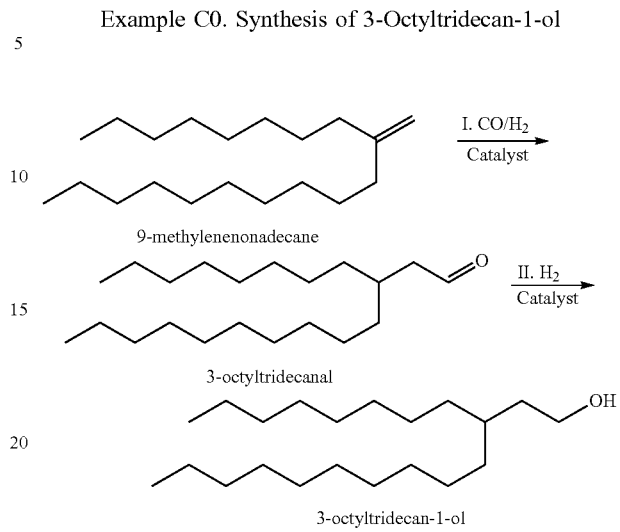

9-methylenenonadecane 3-octyltridecanal 3-octyltridecan-1-ol

C0-I: Hydroformylation of 9-Methylenenonadecane

Into a 1-gallon autoclave equipped with mechanical stirrer, 3.24 grams of (acetylacetonato)dicarbonylrhodium and 4.87 grams of triphenyl phosphine (together "Catalyst") was mixed with 2000 grams of the 9-methylenenonadecane-containing dimer product made in Step A1 above to form a slurry. The reaction system was nitrogen purged and then purged with syngas (1:1 molar ratio $H_2$:CO). The autoclave was pressurized by syngas to 510 psig (3516 kPa, gauge pressure) at 26° C., where agitation begun. Under agitation and constant pressure, temperature was then raised from 26° C. to 100° C. Syngas pressure inside the autoclave was then raised to 700 psig (4826 kPa, gauge pressure) at this temperature and held under constant pressure and temperature for 18 hours before it was depressurized. The reaction product mixture, a dark liquid, was then discharged and filtered to remove solid particles and obtain a carbonyl product mixture. Olefin conversion in this step was measured to be 92.1% with selectivity to C21 carbonyl product estimated at 99%. Infrared absorption spectra of the carbonyl product mixture with an overlay of that of the 9-methylenenonadecane-containing dimer product made in Step A1 showed the formation of a peak at 1729.83 cm-1, indicating the formation of an aldehyde.

C0-II: Hydrogenation of the Carbonyl Product Mixture

Into a 1-gallon autoclave equipped with mechanical stirrer, the carbonyl product mixture made in C0-I above and 27.5 grams of Pt/C catalyst were charged to make a slurry. The autoclave was first purged three times with nitrogen. Next, the autoclave was pressured up with 100% $H_2$ to 500 psig (3447 kPa, gauge pressure) by $H_2$ and the temperature increased to 50° C. The pressure and temperature were then slowly ramped to 100° C. and 1500 psig (10,342 kPa, gauge pressure) over 2 hours. Then, the pressure and temperature was finally increased to 150° C. and 2250 psig (15,513 kPa, gauge pressure) over one hour. The reactor was held at these conditions for 72 hours and then depressurized. The resultant slurry was filtered by vacuum filtration to obtain a crude alcohol mixture. Extent of hydrogenation was measured to be 97.9% with a yield of heavy fractions (fractions having normal boiling points higher than that of 3-octyltridecan-1-ol) at 8.8%.

C0-III: Distillation to Obtain High-Purity 3-Octyltridecan-1-Ol

The crude alcohol mixture produced from C0-II above was distilled to remove light fractions (fractions having normal boiling points lower than that of 3-octyltridecan-1-ol, such as 9-methylnonadecane) and undesired heavy fractions from the hydrogenated alcohol product to produce a high-purity fraction of 3-octyltridecan-1-ol (the "C21-alcohol"). The C21-alcohol purity was measured to be 98.2 wt %, with the balance being predominantly 9-methylnonadecane resulting from the hydrogenation in step C0-II of the residual 9-methylenenonadecane from step C0-I.

The C21-alcohol was measured to have the following properties: a KV100 of 4.18 cSt, a KV40 of 31.4 cSt, a viscosity index of −60.4, a flash point determined pursuant to ASTM D93 of 193° C., a density determined pursuant to ASTM D-4052 of 0.84 gram·cm$^{-3}$, and a refractive index determined pursuant to ASTM D-1218 of 1.453.

Example C1: Synthesis of 3-Octyltridecyl Pentanoate (Comparative)

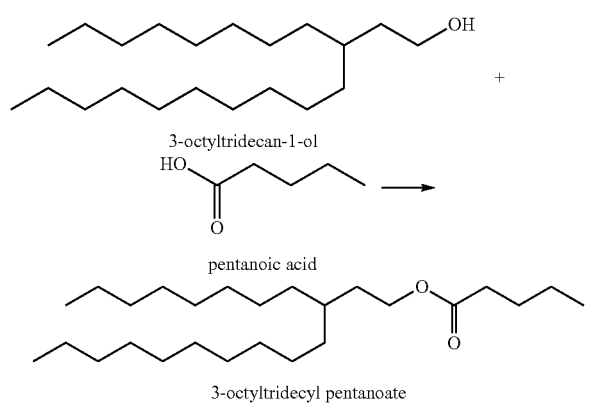

Into a 250 ml glass reactor fitted with an Argon purge was placed the pentanoic acid (20.5 grams, 0.2 moles), 3-octyltridecan-1-ol (30 grams, 0.1 moles) made in Example 1 above (the high-purity 3-octyltridecan-1-ol from step C0-III) and p-toluene sulfonic acid monohydrate (PTSA) (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % aqueous NaHCO$_3$ followed by 250 ml saturated aqueous NaCl. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. Weight of distilled product was 29.7 grams (75%). $^1$H NMR (CDCl$_3$): δ 4.10 (t, 2H, O—CH$_2$—), 2.27 (7, 2H, O=C—CH$_3$), 1.62-1.26 (m, 39H, —CH$_2$—), 0.87 (t, 9H, CH$_3$). $^{13}$C NMR (CDCl$_3$): 171.81, 62.82, 34.56, 34.10, 33.75, 33.58, 32.45, 31.91, 31.28, 30.01, 29.69, 29.68, 29.64, 29.63, 29.35, 27.08, 26.69, 26.53, 22.84, 22.67, 22.27. IR (cm$^{-1}$): 2956, 2924, 2854, 1739, 1466, 1378, 1244, 1171, 1098, 721. The distilled product was used as the fluid for this comparative Example C1.

Example C2: Synthesis of 3-Octyltridecyl Hexanoate (Comparative)

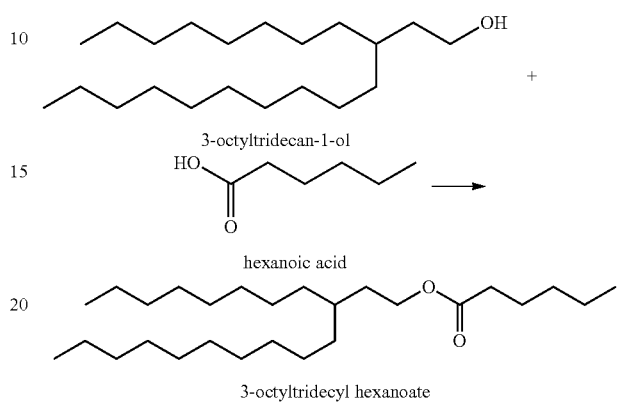

Into a 250 ml glass reactor fitted with an Argon purge was placed the hexanoic acid (23.2 grams, 0.2 moles), 3-octyltridecan-1-ol (30 grams, 0.1 moles) and p-toluene sulfonic acid monohydrate (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % aqueous NaHCO$_3$ followed by 250 ml saturated aqueous NaCl. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. Weight of distilled product was 30.79 grams (74%). The distilled product was characterized by $^1$HNMR. $^1$H NMR (CDCl$_3$): δ 4.10 (t, 2H, O—CH$_2$—), 2.27 (7, 2H, O=C—CH$_3$), 1.62-1.26 (m, 41H, —CH$_2$—), 0.87 (t, 9H, CH$_3$). $^{13}$C NMR (CDCl$_3$): 173.82, 62.74, 34.62, 34.41, 33.64, 32.47, 31.93, 31.35, 30.07, 29.72, 29.37, 26.53, 24.17, 22.27, 22.34, 14.06, 13.89. IR (cm$^{-1}$): 2956, 2924, 2854, 1739, 1466, 1378, 1244, 1171, 1098, 721. The distilled product was used as the fluid for this comparative Example C2.

Example C3: Synthesis of 3-Octyltridecyl Octanoate (Comparative)

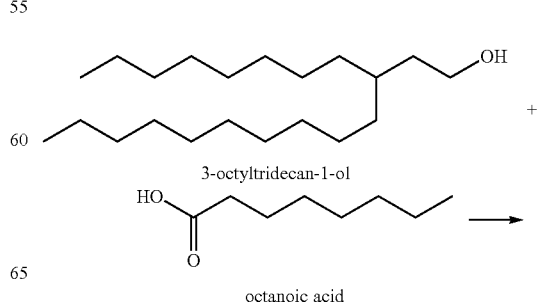

-continued

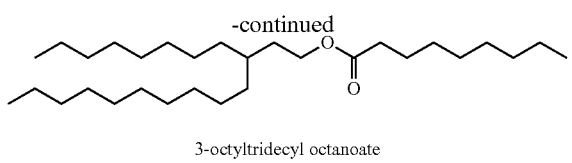

3-octyltridecyl octanoate

Into a 250 ml glass reactor fitted with an Argon purge was placed the octanoic acid (28.4 grams, 0.2 moles), 3-octyl-tridecan-1-ol (30 grams, 0.1 moles) and p-toluene sulfonic acid monohydrate (PTSA) (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10% aqueous $NaHCO_3$ followed by 250 ml saturated aqueous NaCl. The ethyl acetate solution was dried over $MgSO_4$ and then filtered. The ethyl acetate was removed on the rotary evaporator from the solution. The residue from the rotary evaporator was placed on a Kugelrohr vacuum distillation apparatus where the ester was distilled. Weight of distilled product was 32.85 grams (75%). $^1$H NMR ($CDCl_3$): δ 3.96 (d, 2H, O—$CH_2$—), 2.31 (t, 2H, O=C—$CH_3$), 1.61 (m, 3H, —CH—, $CH_2$) 1.31 (m, 42H, —$CH_2$—), 0.87 (t, 9H, $CH_3$). $^{13}$C NMR ($CDCl_3$): 173.90, 62.84, 34.57, 34.43, 33.58, 32.45, 31.92, 31.68, 29.70, 29.69, 29.66, 29.37, 29.14, 26.54, 25.02, 22.69, 22.60, 14.09. IR ($cm^{-1}$): 29.56, 2924, 2854, 1738, 1466, 1377, 1167, 1104, 722. The distilled product was used as the fluid of this comparative Example C3.

Example C4: Polyalpha-olefin (PAO) SpectraSyn Plus™ 3.6 (Comparative)

An API Group IV base stock, a polyalpha-olefin base stock having a KV100 of about 3.6 cSt, available with the trademark SpectraSyn Plus™ 3.6 from ExxonMobil Chemical Company having an address at 5200 Bayway Drive, Baytown, U.S.A., was used as the fluid for this comparative Example C4.

Example C5: Polyalpha-olefin (PAO) SpectraSyn™ 4.0 (Comparative)

An API Group IV base stock, a polyalpha-olefin base stock having a KV100 of about 4.0 cSt, available with the trademark SpectraSyn Plus™ 4.0 from ExxonMobil Chemical Company having an address at 5200 Bayway Drive, Baytown, U.S.A., was used as the fluid for this comparative Example C5.

Part D. Discussions of the Examples

The kinematic viscosity (KV) of the liquid product was determined pursuant to ASTM standards D-445 and reported at temperatures of 100° C. (KV100) and 40° C. (KV40). The viscosity index (VI) was determined according to ASTM standard D-2270 using the measured kinematic viscosities for each product. The final ester products of Examples B1, B2, and B3 were evaluated as synthetic base stocks. Additional properties evaluated are Noack volatility as determined by thermal gravimetric analysis (TGA) expressed as percentage of weight loss during the measurement, oxidation stability in air expressed as oxidation-onset-temperature ("OOT"). Pressure differential scanning calorimetry ("PDSC") was used to determine the oxidation stability of the bases stocks. A DuPont (TA Instruments) DSC model 2920 with a pressure cell was used for all measurements. The cell was well calibrated for temperature (+/–0.3° C.) and heat flow (better than 1%) and checked for reproducibility daily with a quality control standard for temperature and heat response. The error of these measurements is within 1-2 minutes for OOT. The present data were obtained from about 6.5+/–0.2 mg samples placed in aluminum pans. In PDSC scan the OOT was determined by heating the sample at rate of 10° C. per minute using pressure of about 100 psi (689 kPa) in air. The OOT data are shown in TABLE I below and FIGS. 2 and 3.

The neo-acid-derived ester fluids of Examples B1, B2, and B3 were evaluated alongside with comparative fluids C1, C2, and C3, as synthetic base stocks and results are shown in TABLE I. Fluids in comparative Examples C1, C2, and C3 are esters derived from gamma-branched alcohols and linear carboxylic acids having similar molecular structures and molecular weights to the fluids of Examples B1, B2, and B3, respectively.

TABLE I

| Fluid of Example | Molecular Weight (g/mole) | KV100 (cSt) | KV40 (cSt) | VI | Noack Volatility (TGA, wt %) | OOT (PDSC, ° C.) |
|---|---|---|---|---|---|---|
| B1 | 396.4 | 2.98 | 11.5 | 112 | 20.8 | 203.27 |
| B2 | 410.7 | 3.18 | 12.6 | 116 | 17.2 | 204.35 |
| B3 | 438.8 | 3.42 | 13.9 | 122 | 11.2 | 204.18 |
| C1 | 396.7 | 2.70 | 9.12 | 143 | 15.4 | 198.05 |
| C2 | 410.7 | 2.84 | 9.77 | 145 | 11.4 | 199.16 |
| C3 | 438.8 | 3.18 | 11.5 | 151 | 7.9 | 200.82 |

To compare selective neo-acid-derived esters with gamma-branched C21-alcohol based esters, fluids of molecules having similar molecular weight were prepared in the above Examples B1-B3 and comparative Examples C1-C3. Structures of the esters are further provided in TABLE II below. As can be seen, esters of Examples B1 and C1 have the same molecular weight; so do esters of Examples B2 and C2; and esters of Examples B3 and C3.

TABLE II
Inventive Example No.
B1
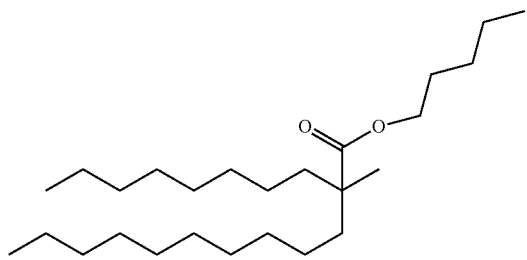
pentyl 2-methyl-2-octyldodecanoate
Molecular Weight: 396.70
B2
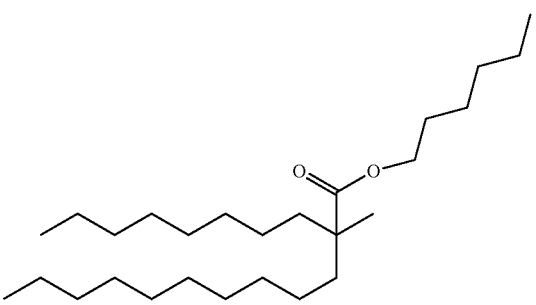
hexyl 2-methyl-2-octyldodecanoate
Molecular Weight: 410.73
B3
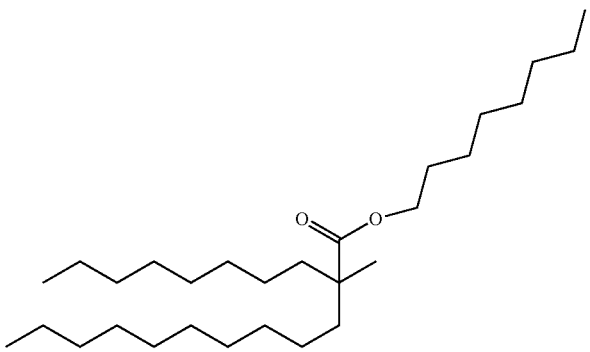
octyl 2-methyl-2-octyldodecanoate
Molecular Weight: 438.78
Comparative Example No.
C1
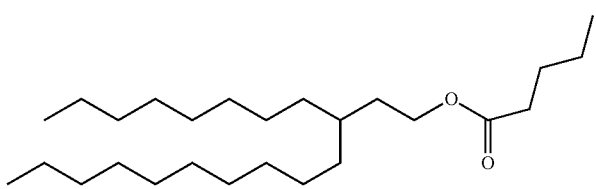
3-octyltridecyl pentanoate
Molecular Weight: 396.70

TABLE II-continued

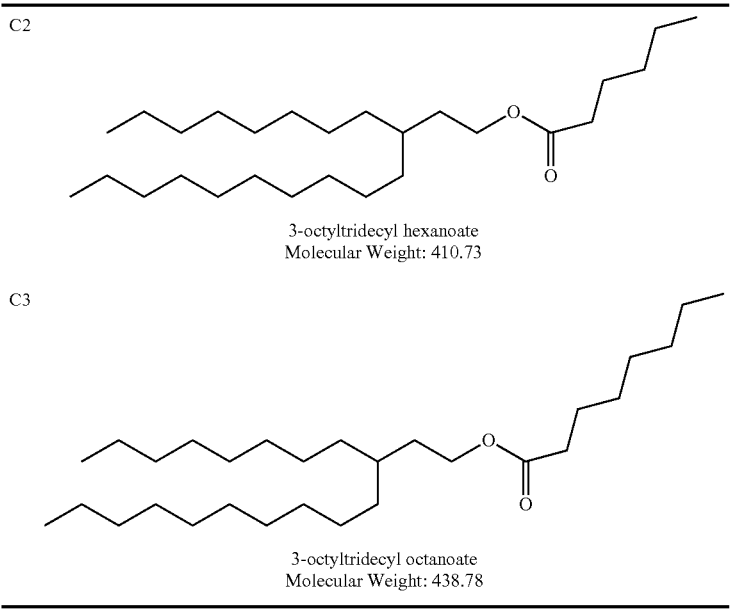

C2
3-octyltridecyl hexanoate
Molecular Weight: 410.73

C3
3-octyltridecyl octanoate
Molecular Weight: 438.78

The viscosity and volatility characteristics of ester fluids of Examples B1, B2, and B3, and PAO base stock Examples C4 and C5 were plotted and results are shown in FIG. 1.

In general, for a fluid useful as a low-viscosity base stock having a KV100 in the range from 2.0 to 4.0 cSt, it is desirable to have a lower KV100 of the fluid, a lower Noack volatility, and a higher viscosity index, all other factors held equal, especially for the purpose of formulating an engine oil.

As can be seen from TABLE I and from FIG. 1, the neo-acid-derived ester fluids of Example B1, B2, and B3 demonstrated low KV100 highly desirable for low-viscosity engine oils. From FIG. 1, it can be seen that the neo-acid-derived ester fluids of this disclosure are directionally better than the PAO base stocks in the KV100 viscosity range from 2.0 to 4.0 cSt in terms of KV100 and Noack volability combination.

Figure 2:
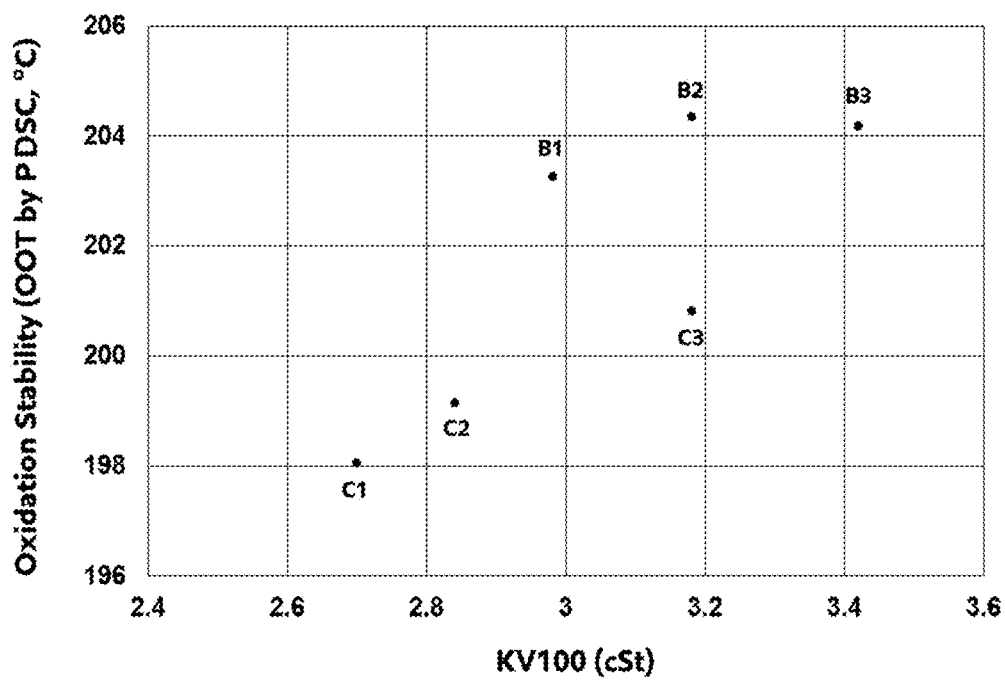
FIG. 2 is a diagram showing and comparing the KV100 and oxidation stability of fluids of inventive Examples B1, B2, and B3 and comparative Examples C1, C2, and C3.

FIG. 2 compares the KV100-oxidation stability characteristics of selective neo-acid-derived esters of Examples B1, B2, and B3 and selective gamma-branched C21-alcohols derived esters of comparative Examples C1, C2, and C3. Oxidation stability is indicated by the OOT temperature measured by PDSC as described above.

The results show that directionally KV100-OOT performance of selective neo-acid-derived esters (Example B1, B2, and B3) is significantly better than selective gamma-branched C20-alcohol-derived esters (Example C1, C2, and C3). The esters of Examples B1, B2, and B3 demonstrated much better oxidation stability compared to the esters of comparative C1, C2, and C3, respectively at similar KV100.

Figure 3:
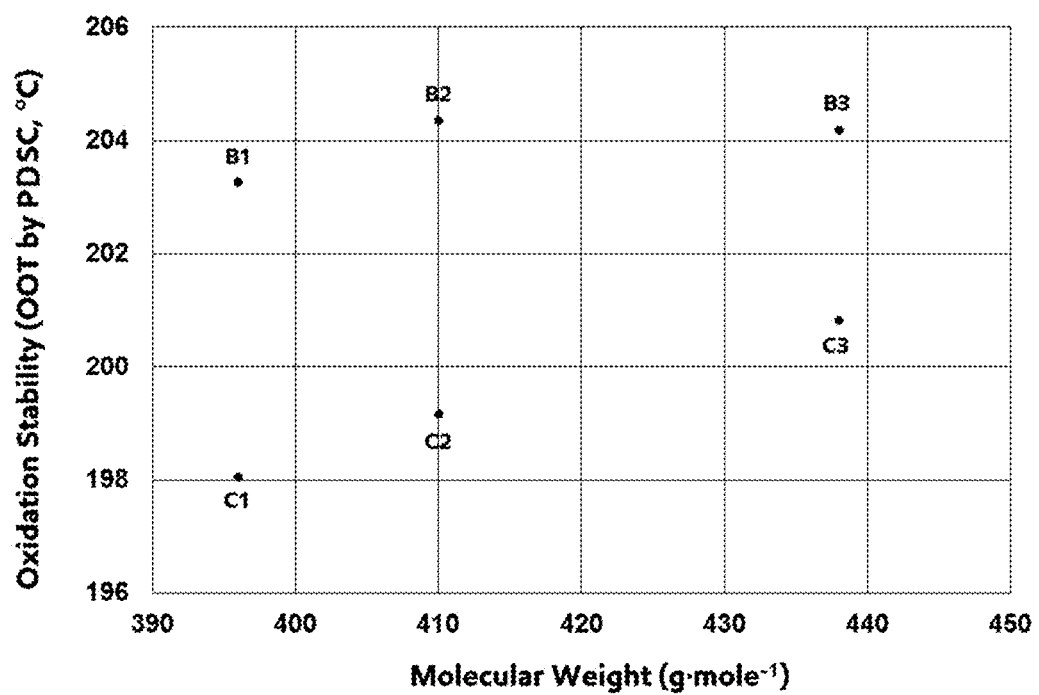
FIG. 3 is a diagram showing and comparing the molecular weight and oxidation stability of fluids of inventive Examples B1, B2, and B3 and comparative Examples C1, C2, and C3.

FIG. 3 compares the molecular weight-OOT characteristics of selective neo-acid-derived esters of Examples B1, B2, and B3 and selective gamma-branched C21-alcohols derived esters of comparative Examples C1, C2, and C3.

The results show that directionally molecular weight-OOT performance of selective neo-acid-derived esters (Example B1, B2, and B3) is significantly better than selective gamma-branched C20-alcohol-derived esters (Example C1, C2, and C3). The esters of Examples B1, B2, and B3 demonstrated much better oxidation stability compared to the esters of comparative C1, C2, and C3, respectively, at the same molecular weight of the ester compound. Thus, the base stocks based on the neo-acid-derived esters of this disclosure tend to be more stable than those based on gamma-alcohol-derived esters having similar molecular weight in environment where the base stock is exposed to elevated temperatures and oxidative environment, e.g., in and around the combustion chamber of an internal combustion engine. Gamma-alcohol-derived esters such as those in comparative Examples C1, C2, and C3 are considered as high-quality base stocks, especially for engine oil lubricants. Nonetheless, the neo-acid-derived esters of this disclosure appear to be even better.

A high oxidation stability of the base stock is highly desirable for a lubricating oil formulation exposed to oxidative environment during use, such as an automotive engine oil. Higher oxidation stability of the base stock translates to higher oxidation stability of the formulation, and hence longer service life and drain interval.

These fluids of Examples B1, B2, and B3 can also be used as plastic (such as PVC) plasticizers and in personal care applications, to name a few.

What is claimed is:

1. A compound having the following formula (F-I):

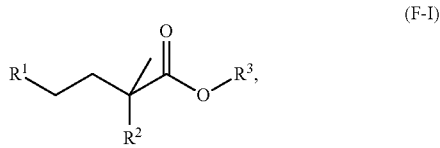

(F-I)

wherein $R^1$ and $R^2$ are each independently a hydrocarbyl group comprising a linear or branched alkyl group of more than ten (10) carbon atoms, or a cyclic group; and $R^3$ is a substituted or unsubstituted hydrocarbyl group.

2. The compound of claim 1, wherein $R^1$ and $R^2$ are each independently a C12 to C30 linear or branched alkyl group.

3. The compound of claim 1, wherein $R^1$ and $R^2$ are each independently a C12 to C30 linear alkyl group.

4. The compound of claim 2, wherein $R^1$ and $R^2$ are each independently selected from n dodecyl, n-tetradecyl, n-hexadecyl, n-octadecyl, n-icosyl, n-docosyl, n-tetracosyl, n-hexacosyl, and n-octacosyl.

5. The compound of claim 4, wherein $R^1$ and $R^2$ are each independently selected from n-dodecyl, and n-tetradecyl.

6. The compound of claim 1, wherein $R^1$ and $R^2$ are each independently a branched alkyl group selected from 2 propylheptanyl, 2-butyloctyl and 3,5-dimethyloctyl.

7. The compound of claim 1, wherein $R^1$ and $R^2$ are identical.

8. The compound of claim 1, wherein $R^3$ is a C1 to C24 group selected from: (a) linear or branched alkyl group, alkylaryl group, aryl group, arylalkyl group, cycloalkyl group, alkylcycloalkyl group, and cycloalkylalkyl group; and (b) substituted derivatives of those in category (a).

9. The compound of claim 8, wherein $R^3$ comprises 1 to 16 carbon atoms in total.

10. The compound of claim 1, wherein $R^3$ is selected from: methyl, ethyl, n-propyl, n-butyl, n-pentyl, n-hexyl, n-heptyl, n-octyl, n-decyl, n-dodecyl, n-tetradecyl, n-hexadecyl, n-octadecyl, n-icosyl, n-docosyl, n-tetracosyl, phenyl, 1-phenylmethyl, 2-phenylmethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

11. The compound of claim 10, wherein $R^3$ is selected from n-pentyl, n-hexyl, n-heptyl, n-octyl, n-nonyl, and n-decyl.

12. The compound of claim 1, which is selected from the following:
phenyl 2-ethyl-2-methylhexanoate; p-tolyl 2-ethyl-2-methylhexanoate; 3,4-dimethylphenyl 2-ethyl-2-methylhexanoate; 3,5-dimethylphenyl 2-ethyl-2-methylhexanoate; 4-ethylphenyl 2-ethyl-2-methylhexanoate; 4-propylphenyl 2-ethyl-2-methylhexanoate; 4-butylphenyl 2-ethyl-2-methylhexanoate; 4-pentylphenyl 2-ethyl-2-methylhexanoate; 4-hexylphenyl 2-ethyl-2-methylhexanoate; 4-heptylphenyl 2-ethyl-2-methylhexanoate; 4-octylphenyl 2-ethyl-2-methylhexanoate; 4-nonylphenyl 2-ethyl-2-methylhexanoate; naphthalen-2-yl 2-ethyl-2-methylhexanoate; 4-benzylphenyl 2-ethyl-2-methylhexanoate; [1,1'-biphenyl]-4-yl 2-ethyl-2-methylhexanoate;
phenyl 2-butyl-2-methyloctanoate; p-tolyl 2-butyl-2-methyloctanoate; 3,4-dimethylphenyl 2-butyl-2-methyloctanoate; 3,5-dimethylphenyl 2-butyl 2-methyloctanoate; 4-ethylphenyl 2-butyl-2-methyloctanoate; 4-propylphenyl 2-butyl-2-methyloctanoate; 4-butylphenyl 2-butyl-2-methyloctanoate; 4-pentylphenyl 2-butyl-2-methyloctanoate; 4-hexylphenyl 2-butyl-2-methyloctanoate; 4-heptylphenyl 2-butyl-2-methyloctanoate; 4-octylphenyl 2-butyl-2-methyloctanoate; 4-nonylphenyl 2-butyl-2-methyloctanoate; naphthalen-2-yl 2-butyl-2-methyloctanoate; 4-benzylphenyl 2-butyl-2-methyloctanoate; [1,1'-biphenyl]-4-yl 2-butyl-2-methyloctanoate;
butyl 2-hexyl-2-methyldecanoate; pentyl 2-hexyl-2-methyldecanoate; hexyl 2-hexyl-2-methyldecanoate; heptyl 2-hexyl-2-methyldecanoate; octyl 2-hexyl-2-methyldecanoate; nonyl 2-hexyl-2-methyldecanoate; decyl 2-hexyl-2-methyldecanoate; dodecyl 2-hexyl-2-methyldecanoate;
butyl 2-dodecyl-2-methylhexadecanoate; pentyl 2-dodecyl-2-methylhexadecanoate; hexyl 2-dodecyl-2-methylhexadecanoate; heptyl 2-dodecyl-2-methylhexadecanoate; octyl 2-dodecyl-2-methylhexadecanoate; nonyl 2-dodecyl-2-methylhexadecanoate; decyl 2-dodecyl-2-methylhexadecanoate; dodecyl 2-dodecyl-2-methylhexadecanoate; phenyl 2-dodecyl-2-methylhexadecanoate; p-tolyl 2-dodecyl-2-methylhexadecanoate; 3,4-dimethylphenyl 2-dodecyl-2-methylhexadecanoate; 3,5-dimethylphenyl 2-dodecyl-2-methylhexadecanoate; 4-ethylphenyl 2-dodecyl-2-methylhexadecanoatee; 4-propylphenyl 2-dodecyl-2-methylhexadecanoate; 4-butylphenyl 2-dodecyl-2-methylhexadecanoate; 4-pentylphenyl 2-dodecyl-2-methylhexadecanoate; 4-heptylphenyl 2-dodecyl-2-methylhexadecanoate; 4-octylphenyl 2-dodecyl-2-methylhexadecanoate; 4-nonylphenyl 2-dodecyl-2-methylhexadecanoate; naphthalen-2-yl 2-dodecyl-2-methylhexadecanoate; 4-benzylphenyl 2-dodecyl-2-methylhexadecanoate; and [1,1'-biphenyl]-4-yl 2-dodecyl-2-methylhexadecanoate.

13. A lubricating oil composition comprising a compound having the following formula (F-I):

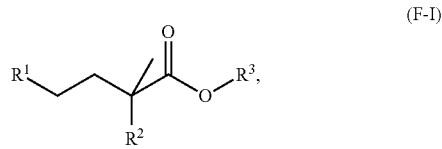

wherein $R^1$ and $R^2$ are each independently a hydrocarbyl group comprising a linear or branched alkyl group of more than ten (10) carbon atoms, or other hydrocarbyl group; and
$R^3$ is a substituted or unsubstituted hydrocarbyl group.

14. The lubricating oil composition of claim 13, which is a lubricating oil base stock.

15. The lubricating oil composition of claim 14, which consists essentially of one or more compounds having formula (F-I).

16. The lubricating oil composition of claim 14, having a kinematic viscosity at 100° C. as determined pursuant to ASTM D445 in the range from 1 to 40 cSt.

17. The lubricating oil composition of claim 13, which is a lubricating oil formulation comprising a compound having formula (F-I) as a first base stock.

18. The lubricating oil composition of claim 17, wherein the concentration of the first base stock, based on the total weight of the lubricating oil formulation, is in the range from 5 to 95 wt %.

19. A process for making an ester product comprising a compound having the following formula (F-I):

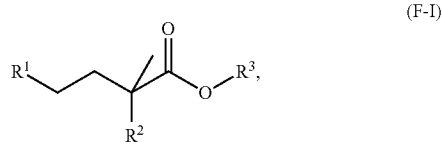

wherein $R^1$ and $R^2$ are each independently a hydrocarbyl group comprising a linear or branched alkyl group of more than ten (10) carbon atoms, or other hydrocarbyl group;
$R^3$ is a substituted or unsubstituted hydrocarbyl group;
the method comprising:
reacting a neo-acid having a formula (F-II) and/or an anhydride thereof with an alcohol having a formula (F-III) below in the presence of an acid catalyst to obtain a reaction mixture, where $R^1$, $R^2$, and $R^3$ correspond to the $R^1$, $R^2$, and $R^3$ in formula (F-I), respectively:

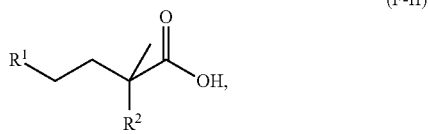

(F-II)

$R^3$—OH (F-III), and obtaining the ester product from the reaction mixture.

20. The process of claim 19, wherein $R^1$ and $R^2$ are each independently a C12 to C30 linear alkyl group.

21. The process of claim 20, wherein $R^1$ and $R^2$ are each independently selected from n-dodecyl, n-tetradecyl, n-hexadecyl, n-octadecyl, n-icosyl, n-docosyl, n-tetracosyl, n-hexacosyl, and n-octacosyl.

22. The process of claim 19, wherein $R^3$ is a C1 to C24 group selected from: (a) linear or branched alkyl group, alkylaryl group, aryl group, arylalkyl group, cycloalkyl group, alkylcycloalkyl group, and cycloalkylalkyl group; and (b) substituted derivatives of those in category (a).

23. The process of claim 22, wherein $R^3$ is selected from: methyl, ethyl, n-propyl, n-butyl, n-pentyl, n-hexyl, n-heptyl, n-octyl, n-decyl, n-dodecyl, n-tetradecyl, n-hexadecyl, n-octadecyl, n-icosyl, n-docosyl, n-tetracosyl, phenyl, 1-phenylmethyl, 2-phenylmethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

24. The process of claim 20, wherein the neo-acid is selected from: 2-dodecyl-2-methylhexadecanoic acid; 2-methyl-2-tetradecyloctadecanoic acid; 2-methyl-2-hexadecylicosanoic acid; and any mixtures of two or more thereof.

25. The process of claim 20, wherein the alcohol is selected from: ethanol; propan-1-ol; butan-1-ol; pentan-1-ol; hexan-1-ol; heptan-1-ol; octan-1-ol; nonan-1-ol; decan-1-ol; undecan-1-ol; dodecan-1-ol; tridecan-1-ol; tetradecan-1-ol; pentadecan-1-ol; hexadecane-1-ol; septadecan-1-ol; octadecan-1-ol; nonadecan-1-ol; icosan-1-ol; benzyl alcohol; 2-phenylethanol; 3-phenyl-propan-1-ol; 4-phenyl-butan-1-ol; 5-phenyl-pentan-1-ol; 6-phenyl-hexan-1-ol; 7-phenyl-heptan-1-ol; 8-phenyl-octan-1-ol; 9-phenyl-nonan-1-ol; and 10-phenyl-decan-1-ol; and any mixtures of two or more thereof.

* * * * *